(12) United States Patent
Throsby et al.

(10) Patent No.: US 9,145,588 B2
(45) Date of Patent: Sep. 29, 2015

(54) GENERATION OF BINDING MOLECULES

(71) Applicant: Merus B.V., Utrecht (NL)

(72) Inventors: Mark Throsby, Utrecht (NL); Ton Logtenberg, Utrecht (NL); John De Kruif, Bilthoven (NL)

(73) Assignee: MERUS BIOPHARMACEUTICALS B.V., Utrecht (NL)

( * ) Notice: Subject to any disclaimer, the term of this patent is extended or adjusted under 35 U.S.C. 154(b) by 0 days.

(21) Appl. No.: 13/627,381

(22) Filed: Sep. 26, 2012

(65) Prior Publication Data

US 2013/0096020 A1    Apr. 18, 2013

Related U.S. Application Data

(60) Provisional application No. 61/539,116, filed on Sep. 26, 2011.

(51) Int. Cl.

| | |
|---|---|
| *C40B 30/04* | (2006.01) |
| *C12Q 1/68* | (2006.01) |
| *C07K 16/00* | (2006.01) |
| *C07K 16/10* | (2006.01) |
| *C07K 16/28* | (2006.01) |
| *C07K 16/46* | (2006.01) |
| *C07K 16/32* | (2006.01) |

(52) U.S. Cl.
CPC .............. *C12Q 1/6869* (2013.01); *C07K 16/00* (2013.01); *C07K 16/1018* (2013.01); *C07K 16/2863* (2013.01); *C07K 16/32* (2013.01); *C07K 16/468* (2013.01); *C07K 2317/565* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 6,596,541 | B2 | 7/2003 | Murphy et al. |
| 7,105,348 | B2 | 9/2006 | Murphy et al. |
| 7,262,028 | B2 | 8/2007 | Van Berkel et al. |
| 7,329,530 | B2 | 2/2008 | Houtzager et al. |
| 7,429,486 | B2 | 9/2008 | Van Berkel et al. |
| 7,579,446 | B2 | 8/2009 | Bakker et al. |
| 7,696,330 | B2 | 4/2010 | Meulen et al. |
| 7,740,852 | B2 | 6/2010 | Bakker et al. |
| 7,777,010 | B2 | 8/2010 | Logtenberg |
| 7,858,086 | B2 | 12/2010 | Geuijen et al. |
| 7,901,919 | B2 | 3/2011 | Houtzager et al. |
| 7,919,257 | B2 | 4/2011 | Hoogenboom et al. |
| 7,927,834 | B2 | 4/2011 | Van Berkel et al. |
| 7,932,360 | B2 | 4/2011 | Van Berkel et al. |

(Continued)

FOREIGN PATENT DOCUMENTS

| | | |
|---|---|---|
| EP | 0814159 A2 | 12/1997 |
| EP | 1439234 A1 | 7/2004 |

(Continued)

OTHER PUBLICATIONS

Pokorna et al. (2008) Genetic Vaccines and Therapy vol. 6 document 4 pp. 1 to 8.*

(Continued)

*Primary Examiner* — Christian Boesen
(74) *Attorney, Agent, or Firm* — Morrison & Foerster LLP

(57) ABSTRACT

Provided are methods for efficiently and comprehensively screening antibody repertoires from B cells to obtain and produce molecules with binding characteristics and functional activities for use in human therapy.

10 Claims, 10 Drawing Sheets

(56) References Cited

U.S. PATENT DOCUMENTS

| | | |
|---|---|---|
| 7,960,518 B2 | 6/2011 | Throsby et al. |
| 7,968,092 B2 | 6/2011 | Throsby et al. |
| 8,052,974 B2 | 11/2011 | Throsby et al. |
| 8,106,170 B2 | 1/2012 | Ter Meulen et al. |
| 8,148,497 B2 | 4/2012 | Bakker et al. |
| 8,192,927 B2 | 6/2012 | Van Den Brink et al. |
| 8,211,431 B2 | 7/2012 | Throsby et al. |
| 8,241,631 B2 | 8/2012 | Throsby et al. |
| 8,268,756 B2 | 9/2012 | Logtenberg et al. |
| 2002/0138857 A1 | 9/2002 | Ghayur |
| 2003/0093820 A1 | 5/2003 | Green et al. |
| 2003/0096225 A1 | 5/2003 | Logtenberg |
| 2005/0170398 A1 | 8/2005 | Van Berkel et al. |
| 2006/0015949 A1 | 1/2006 | Lonberg et al. |
| 2006/0015957 A1 | 1/2006 | Lonberg et al. |
| 2006/0257397 A1 | 11/2006 | Throsby et al. |
| 2007/0280945 A1 | 12/2007 | Stevens et al. |
| 2008/0070799 A1 | 3/2008 | Bakker et al. |
| 2009/0054254 A1 | 2/2009 | Throsby et al. |
| 2009/0130652 A1 | 5/2009 | Throsby et al. |
| 2009/0181855 A1 | 7/2009 | Vasquez et al. |
| 2010/0069614 A1 | 3/2010 | Houtzager et al. |
| 2010/0146647 A1 | 6/2010 | Logtenberg et al. |
| 2010/0172917 A1 | 7/2010 | Ter Meulen et al. |
| 2010/0297153 A1 | 11/2010 | Geuijen et al. |
| 2010/0310572 A1 | 12/2010 | Bakker et al. |
| 2010/0310586 A1 | 12/2010 | Dolcetti et al. |
| 2010/0331527 A1 | 12/2010 | Davis et al. |
| 2011/0177073 A1 | 7/2011 | Van Berkel et al. |
| 2011/0195454 A1 | 8/2011 | McWhirter et al. |
| 2011/0268739 A1 | 11/2011 | Throsby et al. |
| 2012/0021409 A1 | 1/2012 | McWhirter et al. |
| 2012/0039898 A1 | 2/2012 | Throsby et al. |
| 2012/0058907 A1 | 3/2012 | Logtenberg et al. |
| 2012/0076794 A1 | 3/2012 | Throsby et al. |
| 2012/0093823 A1 | 4/2012 | Van Den Brink et al. |
| 2012/0141493 A1 | 6/2012 | Throsby et al. |
| 2012/0177637 A1 | 7/2012 | Hoogenboom et al. |
| 2012/0192300 A1 | 7/2012 | Babb et al. |
| 2012/0276115 A1 | 11/2012 | Van Den Brink et al. |
| 2012/0315278 A1 | 12/2012 | Throsby et al. |

FOREIGN PATENT DOCUMENTS

| | | |
|---|---|---|
| EP | 2147594 B1 | 1/2010 |
| JP | 2006-109711 | 4/2006 |
| WO | 94/02602 A1 | 2/1994 |
| WO | 98/50431 A2 | 11/1998 |
| WO | 98/52976 A1 | 11/1998 |
| WO | 02/066630 A1 | 8/2002 |
| WO | 03/052416 A2 | 6/2003 |
| WO | 2004/009618 A2 | 1/2004 |
| WO | 2004/106375 A1 | 12/2004 |
| WO | 2005/068622 A2 | 7/2005 |
| WO | 2006/117699 A2 | 11/2006 |
| WO | 2008/054606 A2 | 5/2008 |
| WO | 2008/076379 A2 | 6/2008 |
| WO | 2009/100896 A1 | 8/2009 |
| WO | 2009/157771 A2 | 12/2009 |
| WO | 2010/136598 A1 | 12/2010 |
| WO | 2011/097603 A1 | 8/2011 |
| WO | 2011/146514 A2 | 11/2011 |

OTHER PUBLICATIONS

Carter, Paul, "Bispecific human IgG by design," Journal of Immunological Methods, vol. 248:7-15 (2001).

Dechiara, Thomas M. et al., "VelociMouse: Fully ES Cell-Derived F0-Generation Mice Obtained from the Injection of ES Cells into Eight-Cell-Stage Embryos," Gene Knockout Protocols: Second Edition, Ralf Kuhn (Ed.), Humana Press, vol. 530, Chapter 16, pp. 311-324 (2009).

Fecteau, Jessie F. et al., "A New Memory CD27 IgG+ B Cell Population in Peripheral Blood Expressing VH Genes with Low Frequency of Somatic Mutation," The Journal of Immunology, vol. 177:3728-3736 (2006).

GenBank Accession No. DQ187586-1, Protein ID ABA26122.1, Rabquer, B.J. et al., "Differential variable gene usage between pneumococcal polysaccharide specific B cells isolated 5-10 days and 4-6 weeks post-vaccination," 1 page (2005).

Logtenberg, Ton, "Antibody cocktails: next-generation biopharmaceuticals with improved potency," Trends in Biotechnology, vol. 25(9):390-394 (2007).

Murphy, Kenneth, "The Development and Survival of Lymphocytes," Janeway's Immunobioloby, 8th Edition, Taylor & Francis, Chapter 8, pp. 275-290 (2011).

Merus, "MeMo—the ingenious mouse, for improved antibody therapeutics," www.merus.nl, 3 pages (2011).

Attaelmannan, Mohammed et al., "Understanding and Identifying Monoclonal Gammopathies," Clinical Chemistry, vol. 46(8B):1230-1238 (2000).

Aucouturier, Pierre et al., "Monoclonal Ig L Chain and L Chain V Domain Fragment Crystallization in Myeloma-Associated Fanconi's Syndrome," The Journal of Immunology, vol. 150(8):3561-3568 (1993).

Bogen, Bjarne et al., "A rearranged lambda 2 light gene chain retards but does not exclude kappa and lambda 1 expression," Eur. J. Immunol., vol. 21:2391-2395 (1991).

Bruggemann, Marianne et al., "A repertoire of monoclonal antibodies with human heavy chains from transgenic mice," Proc. Natl. Acad. Sci. USA, vol. 86:6709-6713 (1989).

Davies, Nicholas P. et al., "Creation of Mice Expressing Human Antibody Light Chains by Introduction of a Yeast Artificial Chromosome Containing the Core Region of the Human Immunoglobulin kappa Locus," Bio/Technology, vol. 11:911-914 (1993).

De Kruif, John et al., "Human Immunoglobulin Repertoires against Tetanus Toxoid Contain a Large and Diverse Fraction of High-Affinity Promiscuous VH Genes," J. Mol. Biol., vol. 387:548-558 (2009).

De Wildt, Ruud M.T. et al., "Analysis of Heavy and Light Chain Pairings Indicates that Receptor Editing Shapes the Human Antibody Repertoire," J. Mol. Biol., vol. 285:895-901 (1999).

Esposito, Gloria et al., "Phage display of a human antibody against *Clostridium tetani* toxin," Gene, vol. 148:167-168 (1994).

GenBank Accession No. M87478, "Human rearranged IgK mRNA VJC region," 1 page (1994).

Gonzalez-Fermandez, Africa et al., "Analysis of somatic hypermutation in mouse Peyer's patches using immunoglobulin k light-chain transgenes," Proc. Natl. Acad. Sci. USA, vol. 90:9862-9866 (1993).

Goyenechea, Beatriz et al., "Cells strongly expressing Igk transgenes show clonal recruitment of hypermutation: a role for both MAR and the enhancers," The EMBO Journal, vol. 16(13):3987-3994 (1997).

Goyenechea, Beatriz et al., "Modifying the sequence of an immunoglobulin V-gene alters the resulting pattern of hypermutation," Proc. Natl. Acad. Sci. USA, vol. 93:13979-13984 (1996).

Hengstschlager, Markus et al., "A lambda1 transgene under the control of a heavy chain promoter and enhancer does not undergo somatic hypermutation," Eur. J. Immunol., vol. 24:1649-1656 (1994).

Hochedlinger, Konrad et al., "Monoclonal mice generated by nuclear transfer from mature B and T donor cells," Nature, vol. 415:1035-1038 (2002).

Homig-Holzel, Cornelia et al., "Constitutive CD40 signaling in B cells selectively activates the noncanonical NF-kappaB pathway and promotes lymphomagenesis," J. Exp. Med., vol. 205(6):1317-1329 (2008).

ImMunoGeneTics, "CHEB_VK," Detailed results for the IMGT/V-QUEST analysed sequences, 7 pages (2012).

Jakobovits, Aya et al., "From XenoMouse technology to panitumumab, the first fully human antibody product from transgenic mice," Nature Biotechnology, vol. 25(10):1134-1143 (2007).

Jolly, Christopher J. et al., "Rapid methods for the analysis of immunoglobulin gene hypermutation: application to transgenic and gene targeted mice," Nucleic Acids Research, vol. 25(10):1913-1919 (1997).

Kling, Jim, "Big Pharma vies for mice," Nature Biotechnology, vol. 25 (6):613 (2007).

(56) References Cited

OTHER PUBLICATIONS

Klohn, Peter-Christian et al., "IBC's 23rd Annual Antibody Engineering, 10th Annual Antibody Therapeutics International Conferences and the 2012 Annual Meeting of the Antibody Society," mAbs, vol. 5(2):178-201 (2013).
Klotz, Emily L. et al., "Somatic Hypermutation of a lambda2 Transgene Under the Control of the lambda Enhancer or the Heavy Chain Intron Enhancer," The Journal of Immunology, vol. 157:4458-4463 (1996).
Kong, Qingzhong et al., "A lambda 3' Enhancer Drives Active and Untemplated Somatic Hypermutation of a lambda1 Transgene," The Journal of Immunology, vol. 161:294-301 (1998).
Kwaks, Ted H.J. et al., "Employing epigenetics to augment the expression of therapeutic proteins in mammalian cells," Trenneds in Biotechnology, vol. 24(3):137-142 (2006).
Lie, Y.S. et al., "Advances in quantitative PCR technology: 5' nuclease assays," Curr. Opin. Biotechnol., vol. 9 (1):43-48 (1998).
Lonberg, Nils et al., "Antigen-specific human antibodies from mice comprising four distinct genetic modificaitons," Nature, vol. 368:856-859 (1994).
Lonberg, Nils, "Human antibodies from transgenic animals," Nature Biotechnology, vol. 23(9):1117-1125 (2005).
Mao, Xiaohong et al., "Activation of EGFP expression by Cre-mediated excision in a new ROSA26 reporter mouse strain," Blood, vol. 97(1):324-326 (2001).
Mendez, Michael J. et al., "Functional transplant of megabase human immunoglobulin loci recapitulates human antibody response in mice," Nature Genetics, vol. 15:146-156 (1997).
Meyer, Kerstin B. et al., "The importance of the 3'-enhancer region in immunoglobulin kappa gene expression," Nucleic Acids Research, vol. 18(19):5609-5615 (1990).
Nagle, Mike, "Regeneron helps make Sanofi VelocImmune to its 'weak' pipeline," Outsourceing-Pharma.com, 2 pages (2007).
Nemazee, David, "Receptor editing in lymphocyte development and central tolerance," Nature, vol. 6(10):728-740 (2006).
Neuberger, M.S. et al., "Isotype exclusion and transgene down-regulation in immunoglobulin-lambda transgenic mice," Nature, vol. 338:350-352 (1989).
Nissim, Ahuva et al., "Antibody fragments from a 'single pot' phage display library as immunochemical reagents," The EMBO Journal, vol. 13(3):692-698 (1994).
Odegard, Valerie H. et al., "Targeting of somatic hypermutation," Nature Reviews Immunology, vol. 6:573-583 (2006).
Pelanda, Roberta et al., "A Prematurely Expressed Igk Transgene, but Not a VkJk Gene Segment Taragted into the Igk Locus, Can Rescue B Cell Development in lambda5-Deficient Mice," Immunity, vol. 5:229-239 (1996).
Peled, Jonathan U. et al., "The Biochemistry of Somatic Hypermutation," Annu. Rev. Immunol., vol. 26:481-511 (2008).
Popov, Andrei V. et al., "A Human Immunoglobulin lambda Locus Is Similarly Well Expressed in Mice and Humans," J. Exp. Med., vol. 189(10):1611-1619 (1999).
Presta, Leonard G., "Engineering of therapeutic antibodies to minimize immunogenicity and optimize function," Advanced Drug Delivery Reviews, vol. 58:640-656 (2006).
Reddy, S.T. et al., "Monoclonal antibodies isolated without screening by analyzing the variable-gene repertoire of plasma cells," Nature Biotechnology, vol. 28(9):965-969 (2010).
Retter, Marc W. et al., "Receptor Editing Occurs Frequently during Normal B Cell Development," J. Exp. Med., vol. 188(7):1231-1238 (1998).
Rickert, Robert C. et al., "B lymphocyte-specific, Cre-mediated mutagenesis in mice," Nucleic Acids Research, vol. 25(6):1317-1318 (1997).
Roitt, A. , Immunology, Mir, Moscow, pp. 134, 214 (2000).
Scott, Christopher Thomas, "Mice with a human touch," Nature Biotechnology, vol. 25:1075-1077 (2007).
Sasaki, Yoshiteru et al., "Canonical NF-kB Activity, Dispensable for B Cell Development, Replaces BAFF-Receptor Signals and Promotes B Cell Proliferation upon Activation," Immunity, vol. 24:729-739 (2006).
Sharpe, Melanie et al., "Somatic hypermutation of immunoglobulin kappa may depend on sequences 3' of C kappa and occurs on passenger transgenes," The EMBO Journal, vol. 10(8):2139-2145 (1991).
Singer, Maxine et al., "Transcription: The Transfer of DNA Sequence Information to RNA," Genes & Genomes, University Science Books, CA, Chapter 3.2, pp. 134-145 (1991).
Sirac, Christophe et al., "Role of the monoclonal kappa chain V domain and reversibility of renal damage in a transgenic model of acquired Fanconi syndrome," Blood, vol. 108:536-543 (2006).
Smith-Gill, Sandra J. et al., "Contributions of Immunoglobulin Heavy and Light Chains to Antibody Specificity for Lysozyme and Two Haptens," The Journal of Immunology, vol. 139(12):4135-4144 (1987).
Stevens, Sean, "Human Antibody Discovery, VelocImmune—A novel platform," Pharma Focus Asia, Issue 8, pp. 72-74 (2008).
Storb, Ursula et al., "Transgenic Mice with mu and kappa Genes Encoding Antiphosphorylcholine Antibodies," J. Exp. Med., vol. 164:627-641 (1986).
Taylor, Lisa D. et al., "A transgenic mouse that expresses a diversity of human sequence heavy and light chain immunoglobulins," Nucleic Acids Research, vol. 20(23):6287-6295 (1992).
Taylor, Lisa D. et al., "Human immunoglobulin transgenes undergo rearrangement, somatic mutation and class switching in mice that lack endogenous IgM," International Immunology, vol. 6(4):579-591 (1994).
Torres, Raul M. et al., Laboratory Protocols for Conditional Gene Targeting, Oxford University Press, Oxford, Chapters 10-11, pp. 42-53 (1997).
Van Doorn, S.T., Additional post-filing data and letter filed by the patentee, 1 page, dated Jun. 13, 2013.
Weiner, Louis M., "Fully Human Therapeutic Monoclonal Antibodies," J. Immunother., vol. 29(1):1-9 (2006).
Winter, David B. et al., "Insertion of 2 KB of Bacteriophage DNA Between an Immunoglobulin Promoter and Leader Exon Stops Somatic Hypermutation in a kappa Transgene," Molecular Immunology, vol. 34(5):359-366 (1997).
Xiang, Yougui et al., "The Downstream Transcriptional Enhancer, Ed, Positively Regulates Mouse Igk Gene Expression and Somatic Hypermutation," J. Immunol., vol. 180(10):6725-6732 (2008).
Yang, X.W. et al., "Homologous recombination based modification in *Escherichia coli* and germline transmission in transgenic mice of a bacterial artificial chromosome," Nat. Biotechnol., vol. 15(9):859-865 (1997).
Yarilin, A.A., Osnovy Immunologii, [Fundamentals of Immunology], Meditsina, Moscow, p. 194 (1999).
Yarilin, A.A., Osnovy Immunologii, [Fundamentals of Immunology], Meditsina, Moscow, p. 195 (1999).

* cited by examiner

Figure 1

SEQUENCE LISTING

```
<160> NUMBER OF SEQ ID NOS: 158

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgtatcgcct ccctcgcgcc atcag                                            25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctatgcgcct tgccagcccg ctcag                                            25
```

```
<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgtatcgcct ccctcgcgcc atcaggagkt cmagctgcag cagtc              45

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgtatcgcct ccctcgcgcc atcagsagrt ccasctgcag cagtc              45

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgtatcgcct ccctcgcgcc atcagsaggt ccagcthcag cagtc              45

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtatcgcct ccctcgcgcc atcagsagrt ccagctgcaa cagtc              45

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgtatcgcct ccctcgcgcc atcagcakgt ccaactgcag cagcc              45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgtatcgcct ccctcgcgcc atcagcaggc ttatctacag cagtc              45

<210> SEQ ID NO 9
```

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgtatcgcct ccctcgcgcc atcagcagcg tgagctgcag cagtc              45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgtatcgcct ccctcgcgcc atcagcaggt gcagmtgaag sagtc              45

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtatcgcct ccctcgcgcc atcagsakrt gcagcttcag gagtc              45

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgtatcgcct ccctcgcgcc atcaggaggt gaagcttctc cagtc              45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgtatcgcct ccctcgcgcc atcaggaagt gmwgctggtg gagtc              45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtatcgcct ccctcgcgcc atcaggavgt gaagctsgtg gagtc              45

<210> SEQ ID NO 15
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgtatcgcct ccctcgcgcc atcaggaagt gaarmttgag gagtc             45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgtatcgcct ccctcgcgcc atcaggatgt gaacctggaa gtgtc             45

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgtatcgcct ccctcgcgcc atcaggagga gaagctggat gagtc             45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgtatcgcct ccctcgcgcc atcaggaggt gmagctgrtg gaatc             45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgtatcgcct ccctcgcgcc atcagcagrt tactcwgaaa sagtc             45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgtatcgcct ccctcgcgcc atcagcagat ccagttsgtr cagtc             45

<210> SEQ ID NO 21
<211> LENGTH: 45
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 21
cgtatcgcct ccctcgcgcc atcaggaggt gcagcttgtt gagtc         45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
cgtatcgcct ccctcgcgcc atcaggaagt gcagctgttg gagac         45

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
cgtatcgcct ccctcgcgcc atcagsaggt gcagctkgta gagac         45

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
cgtatcgcct ccctcgcgcc atcagcaggt tcacctacaa cagtc         45

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ctatgcgcct tgccagcccg ctcaggagga gacggtgacc gtggtccc      48

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ctatgcgcct tgccagcccg ctcaggagga gactgtgaga gtggtgcc      48

<210> SEQ ID NO 27
<211> LENGTH: 48
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 27
ctatgcgcct tgccagcccg ctcaggcaga gacagtgacc agagtccc           48

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctatgcgcct tgccagcccg ctcaggagga gacggtgact gaggttcc           48

<210> SEQ ID NO 29
<211> LENGTH: 9
<212> TYPE: PRT
<213> ORGANISM: Mus sp.

<400> SEQUENCE: 29

Tyr Ser Asn Tyr Trp Tyr Phe Asp Val
1               5

<210> SEQ ID NO 30
<211> LENGTH: 9
<212> TYPE: PRT
<213> ORGANISM: Mus sp.

<400> SEQUENCE: 30

Gly Gly Leu Arg Gly Tyr Phe Asp Val
1               5

<210> SEQ ID NO 31
<211> LENGTH: 10
<212> TYPE: PRT
<213> ORGANISM: Mus sp.

<400> SEQUENCE: 31

Tyr Asp Ser Asn Tyr Trp Tyr Phe Asp Val
1               5                   10

<210> SEQ ID NO 32
<211> LENGTH: 11
<212> TYPE: PRT
<213> ORGANISM: Mus sp.

<400> SEQUENCE: 32

Thr Tyr Asp Asn Tyr Gly Gly Trp Phe Ala Tyr
1               5                   10

<210> SEQ ID NO 33
<211> LENGTH: 11
<212> TYPE: PRT
<213> ORGANISM: Mus sp.

<400> SEQUENCE: 33

Ala Gly Leu Leu Gly Arg Trp Tyr Phe Asp Val
1               5                   10

<210> SEQ ID NO 34
<211> LENGTH: 6
```

```
<212> TYPE: PRT
<213> ORGANISM: Mus sp.

<400> SEQUENCE: 34

Arg Phe Gly Phe Pro Tyr
1               5

<210> SEQ ID NO 35
<211> LENGTH: 10
<212> TYPE: PRT
<213> ORGANISM: Mus sp.

<400> SEQUENCE: 35

Ala Ile Thr Thr Val Ala Thr Asp Tyr
1               5                   10

<210> SEQ ID NO 36
<211> LENGTH: 8
<212> TYPE: PRT
<213> ORGANISM: Mus sp.

<400> SEQUENCE: 36

Ala Tyr Tyr Tyr Gly Gly Asp Tyr
1               5

<210> SEQ ID NO 37
<211> LENGTH: 12
<212> TYPE: PRT
<213> ORGANISM: Mus sp.

<400> SEQUENCE: 37

Ser Gly Pro Tyr Tyr Ser Ile Arg Tyr Phe Asp Val
1               5                   10

<210> SEQ ID NO 38
<211> LENGTH: 11
<212> TYPE: PRT
<213> ORGANISM: Mus sp.

<400> SEQUENCE: 38

Ser Glu Gly Ser Ser Asn Trp Tyr Phe Asp Val
1               5                   10

<210> SEQ ID NO 39
<211> LENGTH: 9
<212> TYPE: PRT
<213> ORGANISM: Mus sp.

<400> SEQUENCE: 39

Gly Thr Leu Arg Trp Tyr Phe Asp Val
1               5

<210> SEQ ID NO 40
<211> LENGTH: 12
<212> TYPE: PRT
<213> ORGANISM: Mus sp.

<400> SEQUENCE: 40

Asp Phe Tyr Gly Ser Ser Tyr Trp Tyr Phe Asp Val
1               5                   10

<210> SEQ ID NO 41
<211> LENGTH: 9
<212> TYPE: PRT
<213> ORGANISM: Mus sp.
```

<400> SEQUENCE: 41

Asp Asn Trp Asp Trp Tyr Phe Asp Val
1               5

<210> SEQ ID NO 42
<211> LENGTH: 10
<212> TYPE: PRT
<213> ORGANISM: Mus sp.

<400> SEQUENCE: 42

Phe Tyr Asp Tyr Ala Leu Tyr Phe Asp Val
1               5                   10

<210> SEQ ID NO 43
<211> LENGTH: 10
<212> TYPE: PRT
<213> ORGANISM: Mus sp.

<400> SEQUENCE: 43

Gly Asn Tyr Gly Ser Ser Tyr Phe Asp Tyr
1               5                   10

<210> SEQ ID NO 44
<211> LENGTH: 8
<212> TYPE: PRT
<213> ORGANISM: Mus sp.

<400> SEQUENCE: 44

Trp Lys Val Asp Tyr Phe Asp Tyr
1               5

<210> SEQ ID NO 45
<211> LENGTH: 8
<212> TYPE: PRT
<213> ORGANISM: Mus sp.

<400> SEQUENCE: 45

Gly Gly Tyr Trp Tyr Phe Asp Val
1               5

<210> SEQ ID NO 46
<211> LENGTH: 10
<212> TYPE: PRT
<213> ORGANISM: Mus sp.

<400> SEQUENCE: 46

Tyr Lys Ser Asn Tyr Trp Tyr Phe Asp Val
1               5                   10

<210> SEQ ID NO 47
<211> LENGTH: 9
<212> TYPE: PRT
<213> ORGANISM: Mus sp.

<400> SEQUENCE: 47

Leu Leu Pro Tyr Trp Tyr Phe Asp Val
1               5

<210> SEQ ID NO 48
<211> LENGTH: 12
<212> TYPE: PRT
<213> ORGANISM: Mus sp.

<400> SEQUENCE: 48

```
Ser Tyr Tyr Gly Ser Ser Tyr Trp Tyr Phe Asp Val
1               5                   10
```

<210> SEQ ID NO 49
<211> LENGTH: 11
<212> TYPE: PRT
<213> ORGANISM: Mus sp.

<400> SEQUENCE: 49

```
Gly Gly Tyr Tyr Gly Ser Arg Asp Phe Asp Tyr
1               5                   10
```

<210> SEQ ID NO 50
<211> LENGTH: 8
<212> TYPE: PRT
<213> ORGANISM: Mus sp.

<400> SEQUENCE: 50

```
Asp Tyr Asp Trp Tyr Phe Asp Val
1               5
```

<210> SEQ ID NO 51
<211> LENGTH: 11
<212> TYPE: PRT
<213> ORGANISM: Mus sp.

<400> SEQUENCE: 51

```
Thr Tyr Asn Asn Tyr Gly Gly Trp Phe Ala Tyr
1               5                   10
```

<210> SEQ ID NO 52
<211> LENGTH: 11
<212> TYPE: PRT
<213> ORGANISM: Mus sp.

<400> SEQUENCE: 52

```
Gly Gly Leu Tyr Tyr Asp Tyr Pro Phe Ala Tyr
1               5                   10
```

<210> SEQ ID NO 53
<211> LENGTH: 10
<212> TYPE: PRT
<213> ORGANISM: Mus sp.

<400> SEQUENCE: 53

```
Trp Gly Asp Tyr Asp Asp Pro Phe Asp Tyr
1               5                   10
```

<210> SEQ ID NO 54
<211> LENGTH: 12
<212> TYPE: PRT
<213> ORGANISM: Mus sp.

<400> SEQUENCE: 54

```
Asp Tyr Tyr Gly Ser Ser Tyr Trp Tyr Phe Asp Val
1               5                   10
```

<210> SEQ ID NO 55
<211> LENGTH: 4
<212> TYPE: PRT
<213> ORGANISM: Mus sp.

<400> SEQUENCE: 55

```
Glu Ala Thr Tyr
```

<210> SEQ ID NO 56
<211> LENGTH: 10
<212> TYPE: PRT
<213> ORGANISM: Mus sp.

<400> SEQUENCE: 56

Tyr Gly Ser Ser Tyr Trp Tyr Phe Asp Val
1               5                   10

<210> SEQ ID NO 57
<211> LENGTH: 11
<212> TYPE: PRT
<213> ORGANISM: Mus sp.

<400> SEQUENCE: 57

Trp Gly Tyr Gly Ser Lys Asp Ala Met Asp Tyr
1               5                   10

<210> SEQ ID NO 58
<211> LENGTH: 11
<212> TYPE: PRT
<213> ORGANISM: Mus sp.

<400> SEQUENCE: 58

Trp Gly Arg Glu Leu Gly Asn Tyr Phe Asp Tyr
1               5                   10

<210> SEQ ID NO 59
<211> LENGTH: 9
<212> TYPE: PRT
<213> ORGANISM: Mus sp.

<400> SEQUENCE: 59

Tyr Gly Asn Tyr Trp Tyr Phe Asp Val
1               5

<210> SEQ ID NO 60
<211> LENGTH: 12
<212> TYPE: PRT
<213> ORGANISM: Mus sp.

<400> SEQUENCE: 60

Thr Val Thr Thr Gly Ile Tyr Tyr Ala Met Asp Tyr
1               5                   10

<210> SEQ ID NO 61
<211> LENGTH: 13
<212> TYPE: PRT
<213> ORGANISM: Mus sp.

<400> SEQUENCE: 61

His Tyr Tyr Ser Asn Tyr Val Trp Trp Tyr Phe Asp Val
1               5                   10

<210> SEQ ID NO 62
<211> LENGTH: 9
<212> TYPE: PRT
<213> ORGANISM: Mus sp.

<400> SEQUENCE: 62

Gly Ala Leu Arg Gly Tyr Phe Asp Val
1               5

```
<210> SEQ ID NO 63
<211> LENGTH: 10
<212> TYPE: PRT
<213> ORGANISM: Mus sp.

<400> SEQUENCE: 63

His Tyr Tyr Gly Ser Thr Trp Phe Ala Tyr
1               5                   10

<210> SEQ ID NO 64
<211> LENGTH: 9
<212> TYPE: PRT
<213> ORGANISM: Mus sp.

<400> SEQUENCE: 64

Leu Gly Ala Tyr Gly Asn Phe Asp Tyr
1               5

<210> SEQ ID NO 65
<211> LENGTH: 5
<212> TYPE: PRT
<213> ORGANISM: Mus sp.

<400> SEQUENCE: 65

Arg Glu Phe Ala Tyr
1               5

<210> SEQ ID NO 66
<211> LENGTH: 8
<212> TYPE: PRT
<213> ORGANISM: Mus sp.

<400> SEQUENCE: 66

Glu Ala Ala Tyr Tyr Phe Asp Tyr
1               5

<210> SEQ ID NO 67
<211> LENGTH: 9
<212> TYPE: PRT
<213> ORGANISM: Mus sp.

<400> SEQUENCE: 67

Gly Ser Leu Arg Gly Tyr Phe Asp Val
1               5

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cgtatcgcct ccctcgcgcc atcagggg                                          28

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
```

```
tgatgggggt gttgttttgg                                          20
```

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
cagggccag tggatagac                                            19
```

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

```
gcccttgacc aggcatcc                                            18
```

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

```
ctggacaggg atccagagtt c                                        21
```

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73

```
ctatgcgcct tgccagcccg ctcagtgatg ggggtgttgt tttgg              45
```

<210> SEQ ID NO 74
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

```
ctatgcgcct tgccagcccg ctcagcaggg gccagtggat agac               44
```

<210> SEQ ID NO 75
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75

```
ctatgcgcct tgccagcccg ctcaggccct tgaccaggca tcc                43
```

<210> SEQ ID NO 76
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ctatgcgcct tgccagcccg ctcagctgga cagggatcca gagttc          46

<210> SEQ ID NO 77
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aagcagtggt atcaacgcag agtggccatt acggccggg                  39

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aagcagtggt atcaacgcag agtggg                                26

<210> SEQ ID NO 79
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgtatcgcct ccctcgcgcc atcagaagca gtggtatcaa cgcagagt        48

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aagcagtggt atcaacgcag agt                                   23

<210> SEQ ID NO 81
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggccattacg gcc                                              13

<210> SEQ ID NO 82
<211> LENGTH: 10
<212> TYPE: PRT
<213> ORGANISM: Mus sp.

<400> SEQUENCE: 82

His Tyr Ser Asp Tyr Pro Tyr Phe Asp Tyr
1               5                   10

<210> SEQ ID NO 83
<211> LENGTH: 10
<212> TYPE: PRT
<213> ORGANISM: Mus sp.

<400> SEQUENCE: 83

Tyr Gly Asp Tyr Ile Asn Asn Val Asp Tyr
1               5                   10

<210> SEQ ID NO 84
<211> LENGTH: 7
<212> TYPE: PRT
<213> ORGANISM: Mus sp.

<400> SEQUENCE: 84

Gly Phe Tyr Gly Tyr Asp Phe
1               5

<210> SEQ ID NO 85
<211> LENGTH: 12
<212> TYPE: PRT
<213> ORGANISM: Mus sp.

<400> SEQUENCE: 85

Leu Asp Thr Ile Val Glu Asp Trp Tyr Leu Asp Val
1               5                   10

<210> SEQ ID NO 86
<211> LENGTH: 12
<212> TYPE: PRT
<213> ORGANISM: Mus sp.

<400> SEQUENCE: 86

Leu Asp Thr Val Val Glu Asp Trp Tyr Phe Asp Val
1               5                   10

<210> SEQ ID NO 87
<211> LENGTH: 10
<212> TYPE: PRT
<213> ORGANISM: Mus sp.

<400> SEQUENCE: 87

Tyr Gly Asp Tyr Ser Asn Tyr Val Asp Tyr
1               5                   10

<210> SEQ ID NO 88
<211> LENGTH: 11
<212> TYPE: PRT
<213> ORGANISM: Mus sp.

<400> SEQUENCE: 88

Thr Arg Gln Phe Arg Leu Arg Asp Phe Asp Tyr
1               5                   10

<210> SEQ ID NO 89

```
<211> LENGTH: 13
<212> TYPE: PRT
<213> ORGANISM: Mus sp.

<400> SEQUENCE: 89

Phe Asp Tyr Gly Ser Thr Gln Asp Tyr Ala Met Asp Tyr
1               5                   10

<210> SEQ ID NO 90
<211> LENGTH: 11
<212> TYPE: PRT
<213> ORGANISM: Mus sp.

<400> SEQUENCE: 90

Ser Gly Asn Tyr Asp Phe Tyr Pro Met Asp Tyr
1               5                   10

<210> SEQ ID NO 91
<211> LENGTH: 5
<212> TYPE: PRT
<213> ORGANISM: Mus sp.

<400> SEQUENCE: 91

Arg Leu Val Glu Tyr
1               5

<210> SEQ ID NO 92
<211> LENGTH: 10
<212> TYPE: PRT
<213> ORGANISM: Mus sp.

<400> SEQUENCE: 92

Tyr Gly Asp Tyr Ser Asn Asn Val Asp Tyr
1               5                   10

<210> SEQ ID NO 93
<211> LENGTH: 10
<212> TYPE: PRT
<213> ORGANISM: Mus sp.

<400> SEQUENCE: 93

Leu Asp Asp Gly Tyr Pro Trp Phe Ala Tyr
1               5                   10

<210> SEQ ID NO 94
<211> LENGTH: 14
<212> TYPE: PRT
<213> ORGANISM: Mus sp.

<400> SEQUENCE: 94

Leu Ser Asp Tyr Gly Ser Ser Ala Tyr Leu Tyr Leu Asp Val
1               5                   10

<210> SEQ ID NO 95
<211> LENGTH: 14
<212> TYPE: PRT
<213> ORGANISM: Mus sp.

<400> SEQUENCE: 95

Gln Val Asp Tyr Tyr Gly Ser Ser Tyr Trp Tyr Phe Asp Val
1               5                   10

<210> SEQ ID NO 96
<211> LENGTH: 12
<212> TYPE: PRT
```

```
<213> ORGANISM: Mus sp.

<400> SEQUENCE: 96

Leu Gly Tyr Gly Ser Ser Tyr Leu Tyr Phe Asp Val
1               5                   10

<210> SEQ ID NO 97
<211> LENGTH: 12
<212> TYPE: PRT
<213> ORGANISM: Mus sp.

<400> SEQUENCE: 97

Leu Gly Tyr Gly Ser Ile Tyr Leu Tyr Phe Asp Val
1               5                   10

<210> SEQ ID NO 98
<211> LENGTH: 14
<212> TYPE: PRT
<213> ORGANISM: Mus sp.

<400> SEQUENCE: 98

Leu Thr Asp Tyr Gly Ser Gly Thr Tyr Trp Phe Phe Asp Val
1               5                   10

<210> SEQ ID NO 99
<211> LENGTH: 14
<212> TYPE: PRT
<213> ORGANISM: Mus sp.

<400> SEQUENCE: 99

Leu Asp Tyr Tyr Gly Ser Ser Tyr Gly Trp Tyr Phe Asp Val
1               5                   10

<210> SEQ ID NO 100
<211> LENGTH: 10
<212> TYPE: PRT
<213> ORGANISM: Mus sp.

<400> SEQUENCE: 100

Tyr Gly Asp Tyr Ile Asn Ser Val Asp Tyr
1               5                   10

<210> SEQ ID NO 101
<211> LENGTH: 10
<212> TYPE: PRT
<213> ORGANISM: Mus sp.

<400> SEQUENCE: 101

Tyr Thr Asp Tyr Ile Asn Ser Val Asp Tyr
1               5                   10

<210> SEQ ID NO 102
<211> LENGTH: 12
<212> TYPE: PRT
<213> ORGANISM: Mus sp.

<400> SEQUENCE: 102

Leu Asp Thr Ile Val Glu Asp Trp Tyr Phe Asp Val
1               5                   10

<210> SEQ ID NO 103
<211> LENGTH: 11
<212> TYPE: PRT
<213> ORGANISM: Mus sp.
```

<400> SEQUENCE: 103

Asp Tyr Tyr Gly Ser Ser Tyr Gly Phe Asp Tyr
1               5                   10

<210> SEQ ID NO 104
<211> LENGTH: 10
<212> TYPE: PRT
<213> ORGANISM: Mus sp.

<400> SEQUENCE: 104

Ile Tyr Ser Asn Ser Leu Ile Met Asp Tyr
1               5                   10

<210> SEQ ID NO 105
<211> LENGTH: 12
<212> TYPE: PRT
<213> ORGANISM: Mus sp.

<400> SEQUENCE: 105

Leu Gly Tyr Gly Ser Ser Tyr Trp Tyr Phe Asp Val
1               5                   10

<210> SEQ ID NO 106
<211> LENGTH: 10
<212> TYPE: PRT
<213> ORGANISM: Mus sp.

<400> SEQUENCE: 106

Gly Gly Tyr Tyr Pro Tyr Ala Met Asp Tyr
1               5                   10

<210> SEQ ID NO 107
<211> LENGTH: 10
<212> TYPE: PRT
<213> ORGANISM: Mus sp.

<400> SEQUENCE: 107

Glu Gly Arg Gly Asn Tyr Pro Phe Asp Tyr
1               5                   10

<210> SEQ ID NO 108
<211> LENGTH: 9
<212> TYPE: PRT
<213> ORGANISM: Mus sp.

<400> SEQUENCE: 108

Asp Tyr Ser Tyr Tyr Ala Met Asp Tyr
1               5

<210> SEQ ID NO 109
<211> LENGTH: 16
<212> TYPE: PRT
<213> ORGANISM: Mus sp.

<400> SEQUENCE: 109

Met Arg Leu Tyr Tyr Gly Ile Asp Ser Ser Tyr Trp Tyr Phe Asp Val
1               5                   10                  15

<210> SEQ ID NO 110
<211> LENGTH: 16
<212> TYPE: PRT
<213> ORGANISM: Mus sp.

<400> SEQUENCE: 110

```
Met Arg Leu Phe Tyr Gly Ser Arg Tyr Ser Tyr Trp Tyr Phe Asp Val
1               5                   10                  15
```

<210> SEQ ID NO 111
<211> LENGTH: 11
<212> TYPE: PRT
<213> ORGANISM: Mus sp.

<400> SEQUENCE: 111

```
Ser Tyr Tyr Tyr Gly Ser Arg Glu Ser Asp Tyr
1               5                   10
```

<210> SEQ ID NO 112
<211> LENGTH: 10
<212> TYPE: PRT
<213> ORGANISM: Mus sp.

<400> SEQUENCE: 112

```
Gly Lys Tyr Tyr Pro Tyr Tyr Phe Asp Tyr
1               5                   10
```

<210> SEQ ID NO 113
<211> LENGTH: 6
<212> TYPE: PRT
<213> ORGANISM: Mus sp.

<400> SEQUENCE: 113

```
Trp Gly Ser Ser Gly Tyr
1               5
```

<210> SEQ ID NO 114
<211> LENGTH: 12
<212> TYPE: PRT
<213> ORGANISM: Mus sp.

<400> SEQUENCE: 114

```
Thr Gly Tyr Asn Asn Tyr Gly Ser Arg Phe Ile Tyr
1               5                   10
```

<210> SEQ ID NO 115
<211> LENGTH: 5
<212> TYPE: PRT
<213> ORGANISM: Mus sp.

<400> SEQUENCE: 115

```
Arg Leu Val Asp Tyr
1               5
```

<210> SEQ ID NO 116
<211> LENGTH: 12
<212> TYPE: PRT
<213> ORGANISM: Mus sp.

<400> SEQUENCE: 116

```
Trp Trp Phe Leu Arg Gly Val Tyr Val Met Asp Tyr
1               5                   10
```

<210> SEQ ID NO 117
<211> LENGTH: 12
<212> TYPE: PRT
<213> ORGANISM: Mus sp.

<400> SEQUENCE: 117

```
Thr Gly Tyr Asn Asn Tyr Gly Ser Arg Phe Thr Tyr
1               5                   10
```

```
<210> SEQ ID NO 118
<211> LENGTH: 5
<212> TYPE: PRT
<213> ORGANISM: Mus sp.

<400> SEQUENCE: 118

Arg Leu Ile Glu Tyr
1               5

<210> SEQ ID NO 119
<211> LENGTH: 7
<212> TYPE: PRT
<213> ORGANISM: Mus sp.

<400> SEQUENCE: 119

Gly Asp Trp Tyr Phe Asp Val
1               5

<210> SEQ ID NO 120
<211> LENGTH: 12
<212> TYPE: PRT
<213> ORGANISM: Mus sp.

<400> SEQUENCE: 120

Arg Gln Phe Leu Leu Gly Val Tyr Ala Met Asp Tyr
1               5                   10

<210> SEQ ID NO 121
<211> LENGTH: 12
<212> TYPE: PRT
<213> ORGANISM: Mus sp.

<400> SEQUENCE: 121

Arg His Phe Leu Leu Gly Val Tyr Ala Met Asp Tyr
1               5                   10

<210> SEQ ID NO 122
<211> LENGTH: 9
<212> TYPE: PRT
<213> ORGANISM: Mus sp.

<400> SEQUENCE: 122

Glu Gly Arg Val Thr Thr Leu Asp Tyr
1               5

<210> SEQ ID NO 123
<211> LENGTH: 7
<212> TYPE: PRT
<213> ORGANISM: Mus sp.

<400> SEQUENCE: 123

Gly Asp Trp Tyr Phe Asp Tyr
1               5

<210> SEQ ID NO 124
<211> LENGTH: 16
<212> TYPE: PRT
<213> ORGANISM: Mus sp.

<400> SEQUENCE: 124

Met Arg Leu Phe Tyr Gly Ser Ser Tyr Ser Tyr Trp Tyr Phe Asp Val
1               5                   10                  15
```

```
<210> SEQ ID NO 125
<211> LENGTH: 10
<212> TYPE: PRT
<213> ORGANISM: Mus sp.

<400> SEQUENCE: 125

Gly Ser Gly Tyr Val Tyr Ala Met Asp Tyr
1               5                   10

<210> SEQ ID NO 126
<211> LENGTH: 10
<212> TYPE: PRT
<213> ORGANISM: Mus sp.

<400> SEQUENCE: 126

Gly Thr Thr Ala Tyr Tyr Ala Met Asp Tyr
1               5                   10

<210> SEQ ID NO 127
<211> LENGTH: 12
<212> TYPE: PRT
<213> ORGANISM: Mus sp.

<400> SEQUENCE: 127

Thr Gly Tyr Asn Asn Tyr Gly Ser Arg Phe Ala Tyr
1               5                   10

<210> SEQ ID NO 128
<211> LENGTH: 10
<212> TYPE: PRT
<213> ORGANISM: Mus sp.

<400> SEQUENCE: 128

Gly Lys Tyr Tyr Pro Tyr Tyr Phe Val Tyr
1               5                   10

<210> SEQ ID NO 129
<211> LENGTH: 10
<212> TYPE: PRT
<213> ORGANISM: Mus sp.

<400> SEQUENCE: 129

Gly Thr Thr Ser Tyr Tyr Ala Met Asp Tyr
1               5                   10

<210> SEQ ID NO 130
<211> LENGTH: 10
<212> TYPE: PRT
<213> ORGANISM: Mus sp.

<400> SEQUENCE: 130

Arg Gly Ser Tyr Gly Thr Cys Phe Asp Tyr
1               5                   10

<210> SEQ ID NO 131
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acgagtgcgt aagcagtggt atcaacgcag agt                               33
```

```
<210> SEQ ID NO 132
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acgagtgcgt cagggccag tggatagac                                    29

<210> SEQ ID NO 133
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
acgctcgaca aagcagtggt atcaacgcag agt                              33

<210> SEQ ID NO 134
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
acgctcgaca cagggccag tggatagac                                    29

<210> SEQ ID NO 135
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
agacgcactc aagcagtggt atcaacgcag agt                              33

<210> SEQ ID NO 136
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
agacgcactc cagggccag tggatagac                                    29

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
agcactgtag aagcagtggt atcaacgcag agt                              33

<210> SEQ ID NO 138
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
agcactgtag caggggccag tggatagac                                       29

<210> SEQ ID NO 139
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
atcagacacg aagcagtggt atcaacgcag agt                                  33

<210> SEQ ID NO 140
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
atcagacacg caggggccag tggatagac                                       29

<210> SEQ ID NO 141
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
atatcgcgag aagcagtggt atcaacgcag agt                                  33

<210> SEQ ID NO 142
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
atatcgcgag caggggccag tggatagac                                       29

<210> SEQ ID NO 143
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cgtgtctcta aagcagtggt atcaacgcag agt                                  33

<210> SEQ ID NO 144
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cgtgtctcta caggggccag tggatagac                                    29

<210> SEQ ID NO 145
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ctcgcgtgtc aagcagtggt atcaacgcag agt                               33

<210> SEQ ID NO 146
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ctcgcgtgtc caggggccag tggatagac                                    29

<210> SEQ ID NO 147
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
agcactgtag ggccaccaga ttcttatcag ac                                32

<210> SEQ ID NO 148
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
atcagacacg cagttctgag gccagcacag tg                                32

<210> SEQ ID NO 149
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
tctctatgcg aagcagtggt atcaacgcag agt                               33

<210> SEQ ID NO 150
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 150
tctctatgcg ggccaccaga ttcttatcag ac                                    32

<210> SEQ ID NO 151
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
tgatacgtct aagcagtggt atcaacgcag agt                                   33

<210> SEQ ID NO 152
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tgatacgtct cagttctgag gccagcacag tg                                    32

<210> SEQ ID NO 153
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tcacgtacta aagcagtggt atcaacgcag agt                                   33

<210> SEQ ID NO 154
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
tcacgtacta ggccaccaga ttcttatcag ac                                    32

<210> SEQ ID NO 155
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
cgtctagtac aagcagtggt atcaacgcag agt                                   33

<210> SEQ ID NO 156
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 156
cgtctagtac cagttctgag gccagcacag tg                                   32

<210> SEQ ID NO 157
<211> LENGTH: 206
<212> TYPE: DNA
<213> ORGANISM: Mus sp.
<220> FEATURE:
<221> NAME/KEY: CDS
<222> LOCATION: (3)..(206)

<400> SEQUENCE: 157 ct gtc tct gca gcc aaa aca aca gcc cca tcg gtc tat cca ctg gcc         47
   Val Ser Ala Ala Lys Thr Thr Ala Pro Ser Val Tyr Pro Leu Ala
    1               5                  10                  15 cct gtg tgt gga ggt aca act ggc tcc tcg gtg act cta gga tgc ctg        95
Pro Val Cys Gly Gly Thr Thr Gly Ser Ser Val Thr Leu Gly Cys Leu
             20                  25                  30 gtc aag ggt tat ttc cct gag cca gtg aca ttg acc tgg aac tct gga       143
Val Lys Gly Tyr Phe Pro Glu Pro Val Thr Leu Thr Trp Asn Ser Gly
         35                  40                  45 tcc ctg tcc agt ggt gtg cac acc ttc cca gct ctc ctg cag tct ggc       191
Ser Leu Ser Ser Gly Val His Thr Phe Pro Ala Leu Leu Gln Ser Gly
     50                  55                  60 ctc tac acc ctc agc                                                   206
Leu Tyr Thr Leu Ser
 65

<210> SEQ ID NO 158
<211> LENGTH: 68
<212> TYPE: PRT
<213> ORGANISM: Mus sp.

<400> SEQUENCE: 158

Val Ser Ala Ala Lys Thr Thr Ala Pro Ser Val Tyr Pro Leu Ala Pro
 1               5                  10                  15

Val Cys Gly Gly Thr Thr Gly Ser Ser Val Thr Leu Gly Cys Leu Val
            20                  25                  30

Lys Gly Tyr Phe Pro Glu Pro Val Thr Leu Thr Trp Asn Ser Gly Ser
        35                  40                  45

Leu Ser Ser Gly Val His Thr Phe Pro Ala Leu Leu Gln Ser Gly Leu
    50                  55                  60

Tyr Thr Leu Ser
65
```

GENERATION OF BINDING MOLECULES

RELATED APPLICATIONS

This application claim priority to U.S. Provisional Application No. 61/539,116, entitled "Generation of Binding Molecules", filed Sep. 26, 2011, the entire contents of which are incorporated herein by this reference.

SEQUENCE LISTING

The instant application contains a Sequence Listing which has been submitted in ASCII format via EFS-Web and is hereby incorporated by reference in its entirety. Said ASCII copy, created on Nov. 27, 2012, is named MRX5-004.txt and is 30,662 bytes in size.

BACKGROUND OF THE INVENTION

The ability of the mammalian immune response to generate a large and diverse antibody repertoire in response to antigen has been exploited for a range of applications in diagnostics, therapy and basic research. In particular, monoclonal antibodies, the products of a single B cell clone, have been broadly applied because of their well-defined specificity and ease of production. Typically, monoclonal antibodies or the genetic information encoding monoclonal antibodies with desirable specificities are obtained from the B cells of animals or humans that have been immunized with antigen or infected by pathogens. Alternatively, monoclonal antibodies may be obtained by one of several recombinant-DNA-based methods to construct and screen libraries of antibodies or antibody fragments expressed on the surface of bacteriophages or eukaryotic cells, or from in silica approaches.

Monoclonal antibodies have found increasing use in human therapy for the treatment of a variety of diseases, including for example chronic inflammatory diseases and cancer. The immunogenicity of xenogeneic monoclonal antibodies limits their use in the therapy of human disease. Exposure of patients to xenogeneic antibodies often results in adverse effects or might lead to the neutralization and clearance of the applied antibody, thereby reducing its pharmacological efficacy (Clark, 2000). Administration of humanized or fully human monoclonal antibodies to patients usually diminishes the aforementioned complications, in particular when the amino acid sequences of the antibodies do not contain epitopes that stimulate T cells. Antibodies encoded by non-mutated, human germline heavy and light chain V gene segments containing CDR3 regions devoid of T cell epitopes represent ultimate examples of protein drugs with low immunogenicity (Ruuls et al., 2008; Harding et al., 2010). So, for therapeutic applications, monoclonal antibodies are preferably fully human, non-mutated and contain few or no T cell epitopes to prevent the formation of anti-drug antibodies.

B cells from the blood or lymphoid organs of humans have been used as a source of therapeutic monoclonal antibodies. Since the discovery of the hybridoma technology for immortalization of murine B cells (Kohler et al., 1975) and the realization that this technology could not be readily replicated using human B cells, several alternative methods for the generation of human monoclonal antibodies have been developed. Such methods include transformation of B cells through Epstein-Barr virus infection (Tragiai et al., 2004), short term activation and expansion of human B cells by stimulation with combinations of stimulator cells, antibodies and cytokines (Zubler 1987/Banchereau et al., 1991/Kim et al., 2001/Good et al., 2006/Ettinger et al., 2005) or retrovirus-mediated gene transfer (Kwakkenbos et al., 2010), cloning of antibody V genes from single human B cells by PCR (Wrammert et al., 2010/Meijer et al., 2006), and identification and selection of antigen-specific antibody-secreting B cells by hemolytic plaque assays (Babcook et al., 1996). Human B cell immortalization or activation techniques are compatible with only some stages of B cell maturation and furthermore, due to their low efficiencies (merely 1-3% of B cells) they are not suitable for efficient interrogation of the whole repertoire of specific antibodies generated during a human immune response for antibodies with desired characteristics (Reddy et al., 2011).

Single-cell cloning, a procedure in which single human B cells are plated in microtiter well plates for analysis, has been used to circumvent the low efficiencies associated with procedures that require B cell activation and/or immortalization to obtain human monoclonal antibodies. In this approach, RNA from individual B cells is used to amplify the variable regions of the heavy and light chain (VH, VL) of antibodies by PCR. The VH and VL genes are then inserted into suitable expression vectors for transfection into cell lines and subsequent production of recombinant antibody fragments or full-length IgG (Smith et al., 2009/Tiller et al., 2008). Alternatively, amplified VH and VL genes may be directly used for in vitro transcription and translation to generate minute quantities of antibodies sufficient for binding analysis but nor for assessing functional activity (Jiang et. al., 2006). Using these procedures, the production of recombinant monoclonal antibodies is not limited to distinct B cell populations and does not depend on prior stimulation or immortalization. The major challenge in this approach is the specific amplification of antibody genes by RT-PCR from single cells and the occurrence of cross-contamination during handling of large numbers of PCR reactions. Another practical limitation is the number of individual B cells that can be handled, which is typically restricted to several thousand, preventing extensive sampling of the entire antibody repertoire generated during an immune response. Finally, the method is restricted to the analysis of readily accessible human B cells such as those derived from blood and bone marrow.

Human monoclonal antibodies can also be isolated from recombinant antibody libraries in the laboratory, using one of the platforms for selection that in essence mimics the in vivo antibody response (Hoogenboom, 2005). For example, display technologies exploit large collections of cloned antibody variable regions expressed on the surface of phage particles, bacteria, eukaryotic cells or ribosomes to select for antibodies that bind to antigens of interest (Ponsel et al., 2011/Clackson et al., 1991/Boder et al., 1997/Fuchs et al., 1991/Lee et al., 2007/Chao et al., 2006). The VH and VL regions inserted in these display systems are randomly combined to form collections of antibody binding sites, i.e. fragments of intact IgG antibodies, which require correct folding and assembly in e.g. prokaryotic cells for retrieval by antigen-binding methods. Display methods do not allow the retrieval of antibodies from libraries through functional screening. In display approaches, original pairing of heavy and light chains is abrogated and, in addition, antibody-encoding DNA is lost as a result of the use of restriction enzymes during the cloning procedure. The success of recovering desired antibody specificities with in vitro antibody discovery techniques depends not only on the successful folding and expression of the recombinant antibody fragments in e.g. prokaryotic cells but also on a range of screening parameters used during antibody selection. These include the nature of the display platform, antigen concentration, binding avidity during enrichment, the number of selection rounds, and the design and diversity of the antibody libraries (Hoogenboom 2005/Cobaugh et al., 2008/Persson et al., 2006). Thus, due to experimental procedures, folding requirements for expression of antibody fragments in prokaryotic cells and parameters affecting the success of antibody retrieval during selections, display systems do not permit the comprehensive mining of antibody repertoires and do not allow direct functional screening of human antibodies. Indeed, antigen-specific antibody fragments may be lost during subsequent rounds of antigen selection of phage display libraries (Ravn et al., 2010).

Transgenic mice harboring collections of human antibody genes have been constructed to alleviate some of the restrictions associated with the use of human B cells as starting material for the generation of human monoclonal antibodies (Lonberg 2005). Such mice can be immunized with any antigen and their lymphoid organs are readily accessible for harvesting B cells. Once the transgenic mouse has been immunized, monoclonals can either be obtained through traditional hybridoma generation, by display technologies or using approaches that involve the harvesting, plating and screening of B cells, followed by isolation of mAb genes and cloning into production cell lines.

For the generation of hybridomas, B cells from murine lymphoid organs are harvested and fused with myeloma cells to form immortalized monoclonal antibody-secreting cell lines. The low efficiency of cell fusion in hybridoma formation permits interrogation of only a fraction of the antibody repertoire and is restricted to B cell populations that are amenable to fusion. If a satisfactory hybridoma is not formed, it becomes difficult to obtain the antibody against challenging antigens such as membrane proteins. Thus, increasing the numbers of hybridomas is a crucially important step in screening the repertoire of antigen-specific B cells from immunized mice and obtaining monoclonal antibodies with high affinity, specificity and desired functional activity (Kato et al., 2011/Li et. al., 1994; Crowe, 2009). In the most efficient fusion protocols involving pre-stimulation of B cells and electrofusion, approximately 1 in 1000 B cells fuses successfully with a myeloma cell to become an antibody-secreting hybridoma (Kato et. al., 2011). The hybridoma technology and other B cell immortalization methods interrogate the antibody-producing cells in pre-plasma cell B cell populations, specifically in memory B cells, or in circulating short-lived plasma blasts (Wrammert et al., 2008).

B cells from immunized transgenic mice with human antibody genes may be used to obtain collections of VH and VL regions that are randomly combined to form combinatorial display libraries of human antibody fragments. As argued above, due to experimental procedures, folding requirements for expression of antibody fragments in prokaryotic cells and parameters affecting the success of antibody retrieval during selections, display systems do not permit the comprehensive mining of antibody repertoires and do not allow direct functional screening of human monoclonal antibodies.

High-throughput sequencing has been utilized for sequencing of antibody repertoires derived from bone marrow plasma cells of protein-immunized mice (Reddy et al., 2010). It was found that in the purified plasma cell population, VH and VL repertoires were highly polarized with the most abundant sequences representing 1-10% of the entire repertoire (Reddy et al., 2010). The most abundant VH and VL genes were randomly-paired, expressed as IgG molecules and screened for binding to the immunizing antigen.

A disadvantage of random pairing is that only 4% of the thus generated antibodies were found to bind to the immunizing antigen. These antibodies had low affinities and/or poor expression levels and aggregation was frequently observed. The low proportion of specific antibodies could be improved by pairing VH and VL genes based on their relative frequency in the collection of sequences. In that case, following recombinant expression, approximately 75% of antibodies were found to bind to antigen (Reddy et al., 2010). The disadvantage of VH/VL pairing according to relative frequencies is that collections of V-genes obtained by high throughput sequencing may contain VH and VL sequences that are present in similar frequencies yet are derived from different B cell clones and thus may not represent a natural pair and may not form a functional antibody molecule. Pairing of VH and VL regions based on frequency is therefore inaccurate and may lead to the generation and screening of many antibodies that have mismatched VH/VL pairs encoding low affinity antibodies or antibodies that do not bind to the target of interest. Indeed, it has been shown that VH/VL pairing based on relative frequencies yields a high proportion of modest to low affinity antibodies (Reddy et al., 2010). This implies that VH/VL pairing based on high frequency of VH and VL genes present in large collections of sequences is not predictive for the generation of high affinity antibodies. Thus, such an approach yields only small numbers VH/VL combinations encoding antigen-specific antibodies which were generally found to have low affinities (Reddy et al., 2010).

A further disadvantage of the method reported by Reddy et al. is that it relied on plasma cells as a source of antigen-specific monoclonal antibodies. Plasma cells represent only a small subpopulation of B-lineage cells contributing to antibody diversity generated during an immune response. As a result antigen specific antibodies produced by other B cell populations during an immune response are not retrieved. These populations include short-lived plasma cells, transitional B cells, germinal center B cells and IgM and IgG memory B cells present in lymphoid organs. When comparing antibody repertoires in these various B cell populations, significant changes were observed (Wu, et al., 2010) which implies that a broader antibody repertoire is captured when more B cell populations are included as source for VH/VL in deep sequencing.

Based on the above, it can be concluded that there is a need for antibody generation and selection approaches that facilitate the interrogation of entire antibody repertoires for antibodies encoded by original VH/VL pairs with desirable binding characteristics and functional activities.

SUMMARY OF THE INVENTION

To recapitulate, for selection and screening of the entire repertoire of antibodies produced during an immune response it is necessary to exploit techniques that allow efficient retrieval of antigen-driven, clonally expanded B cells of various phenotypes and subpopulations and/or the genetic information encoding the corresponding antibodies as original VH/VL pairs. The present invention provides a method to efficiently and comprehensively interrogate the broad spectrum of antibodies generated by B cell populations. Preferably, these diverse B cell populations are obtained from transgenic animals, e.g. mice, which harbor human antibody genes to facilitate immunization with any desirable antigen and generate antibodies for therapeutic application in humans. It is most preferred that these transgenic mice have a limited VL repertoire, in particular a single human rearranged VL. The method is independent of B cell immortalization or activation procedures, facilitates screening of antibody repertoires from B cells obtained from essentially all lymphoid organs and does not require analyses of individual B cells. Preferably, to efficiently mine the entire repertoire of antibodies generated during an immune response, B cells from every differentiation stage and lineage and present in relevant lymphoid organs such as lymph nodes, spleen blood and bone marrow are analyzed for the presence of monoclonal antibodies of desired specificity and characteristics such as affinity and functional activity. The method may thus address the entire population of B cells in lymphoid organs or focus on B cells subpopulations that are distinguishable based on phenotypic characteristics such as transitional B cells, memory B cells, short-lived plasma cells and the like. Furthermore, the method allows direct screening of antibodies for binding characteristics as well as functional activity in the relevant antibody format that is representative for eventual application in human therapy. The invention further provides for methods and means for production of these selected antibodies in the desired formats as well as these antibodies and their uses themselves. These uses include arrays as well as pharmaceutical products.

The invention provides a method for producing a defined population of binding molecules, said method comprises at least the following steps: a) providing a population of B cells expressing a limited VL repertoire wherein essentially all of said B cells carry at least one VL, b) obtaining nucleic acids (RNA or DNA) from said B cells, c) optionally, amplification of nucleic acid sequences encoding immunoglobulin heavy chain variable regions in said sample, d) at least partial sequencing of all obtained nucleic acids of step b) or the amplification products of step c), e) performing a frequency analysis of sequences from step d), f) selecting desired VH sequences, g) providing a host cell with at least one vector comprising at least one of said desired VH sequences and/or at least one VL sequence of said limited VL repertoire, h) culturing said host cells and allowing for expression of VH and/or VL polypeptides, i) obtaining said binding molecules. Alternatively, step c) and d) can be replaced or supplemented by the alternative steps c' and d': c') constructing a cDNA library that is screened for VH region specific DNA sequences by probing with a nucleic acid probe specific for VH regions sequences and d') at least partial sequencing of clones containing VH inserts. Where VH or VL is mentioned, functional derivatives and/or fragments thereof are also envisaged.

BRIEF DESCRIPTION OF THE FIGURES

FIG. 1 depicts the 4 mouse CH1 reverse primers and their position within the CH1 region are highlighted (1) Mouse CH1rev0; (2) CH1rev1; (3) CH1rev2; (4) CH1rev3. FIG. 1 discloses SEQ ID NOS 158 and 157, respectively, in order of appearance.

DETAILED DESCRIPTION

Figure 2:
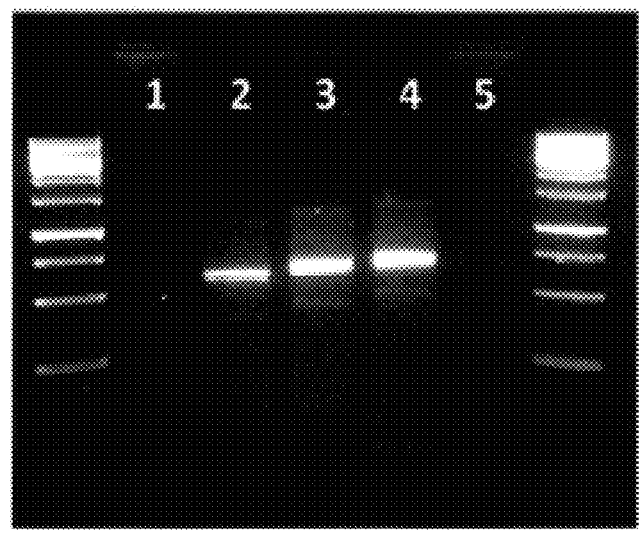
FIG. 2 depicts the VH amplification with forward primer DO_1177 and various CH1 reverse primers. Lane 1: DO_1171; Lane 2: DO_1172; Lane 3: DO_1173; Lane 4: DO_1174; Lane 5: negative control.

The term 'obtaining nucleic acids' as used in step c) herein includes any methods for retrieving the sequence of nucleotides of nucleic acids encoding VH sequences.

The term 'defined population of binding molecules' as used herein refers to at least two binding molecules that bind to at least one selected antigen or epitope of interest. Preferably, the defined population of binding molecules comprises at least a significant portion, preferably at least the majority and most preferably essentially all specific binding molecules directed against the antigen or epitope of interest generated during an immune response. More preferably a population of binding molecules comprises between hundred and several thousand binding molecules, representing a significant portion of unique antigen-specific antibodies present in, e.g., a mouse immunized with said antigen. The population of binding molecules of the present invention may have different specificities and/or affinities; i.e. may bind to different epitopes of the selected antigen or may bind to the same epitope with differing affinities. The term 'binding molecule' as used herein means a molecule comprising a polypeptide containing one or more regions, preferably domains, which bind an epitope on an antigen. In a preferred embodiment, such domains are derived from an antibody.

The term 'antibody' as used herein means a protein containing one or more domains that bind an epitope on an antigen, where such domains are derived from or share sequence homology with the variable region of an antibody. Antibodies are known in the art and include several isotypes, such as IgG1, IgG2, IgG3, IgG4, IgA, IgD, IgE, and IgM. An antibody according to the invention may be any of these isotypes, or a functional derivative and/or fragment of these. Examples of antibodies according to the invention include full length antibodies, antibody fragments, bispecific antibodies, immunoconjugates, and the like. Antibody fragments include Fv, scFv, Fab, Fab', F(ab')$_2$ fragments, and the like. Antibodies according to the invention can be of any origin, including murine, of more than one origin, i.e. chimeric, humanized, or fully human antibodies. Where the term functional fragment and/or derivative is used in this specification it is intended to convey that at least one of the functions, preferably the characterizing functions of the original molecule are retained (in kind not necessarily in amount). Antibody binding is defined in terms of specificity and affinity. The specificity determines which antigen or epitope thereof is bound by the binding domain. The affinity is a measure for the strength of binding to a particular antigen or epitope. Specific binding is defined as binding with affinities ($K_D$) of at least $1 \times 10^{-5}$M, more preferably $1 \times 10^{-7}$M, more preferably higher than $1\times10^{-9}$ M. Typically, monoclonal antibodies for therapeutic application may have affinities of up to $1\times10^{-10}$ M or even higher.

The term 'antigen' as used herein means a substance or molecule that, when introduced into the body, triggers the production of an antibody by the immune system. An antigen, among others, may be derived from pathogenic organisms, tumor cells or other aberrant cells, from haptens, or even from self structures. At the molecular level, an antigen is characterized by its ability to be "bound" by the antigen-binding site of an antibody. In certain aspects of the present invention also mixtures of antigens can be regarded as 'antigen'. An antigen will comprise at least one epitope. The term 'epitope' as used herein means the part of an antigen that is recognized by the immune system, specifically by antibodies, B cells, or T cells. Although epitopes are usually thought to be derived from non-self proteins, sequences derived from the host that can be recognized are also classified as epitopes/antigens.

A 'population of B cells' as used herein may be any collection of B cells. The B cells may be present as a subpopulation of other cells in a sample. It may be derived from one or more individuals from the same or different species. Preferably, the term 'population of B cells' means a group of B cells obtained from at least one animal, preferably obtained from lymphoid organs. In a preferred embodiment, a population of B cells comprises essentially all splenic B cells. In a more preferred embodiment, the population further comprises also essentially all B cells obtained from at least one lymph node. In a most preferred embodiment, the population of B cells comprises B cells obtained from spleen, at least one lymph node, blood and/or bone marrow. In a particularly preferred embodiment, a population of B cells comprises essentially all B cells obtained from one or more lymphoid organs that harbor the B cells that have clonally expanded as a result of antigen stimulation. Methods to obtain such B cell populations are known in the art. Of this population of B cells, essentially all B cells carry at least one VL. In a preferred embodiment, essentially all B cells in the population of B cells express a limited VL repertoire. In a most preferred embodiment, essentially all B cells in the population of B cells carry the same VL.

The term 'limited VL repertoire' used herein means a restricted cohort of VL regions that supports the generation of a robust immune response upon immunization and allows the efficient assembly of original VH/VL pairs with VH regions identified through the construction of heavy chain CDR3 heat maps. In one embodiment the limited VL repertoire comprises no more than 100 different VL regions. When these 100 different VL regions will be matched with a cohort of 100 different, grouped, VH regions it will result in $10^4$ combinations (100 times 100) of VH/VL pairs that can still be screened in functional assays. In a more preferred embodiment, the limited VL repertoire comprises no more than 10, more preferably no more than 3 or 2 different VL regions, thereby further limiting the number of different VH/VL combinations and increasing the frequency of original VH/VL pairs. In the most preferred embodiment, the limited VL repertoire comprises no more than a single VL region. The advantage of a single VL is that all antibodies that are generated upon encounter with an antigen share the same VL and are diversified only in the VH usage. A VL is defined by the particular combination of germline V and J gene segments and CDR3 region and includes somatically mutated variants of said VL. Thus, the population of B cells expressing a limited VL repertoire can mean that essentially no more than 100 VL, or preferably less than 50 VL, or more preferably less than 10, or 3 or 2 VL or most preferably a single VL is expressed. In a preferred embodiment, all VLs in the limited VL repertoire are resistant to DNA rearrangements and/or somatic hypermutations, preferably, the VL have a germline sequence. The preferred germline sequence is a light chain variable region that is frequently used in the human repertoire and has superior ability to pair with many different VH regions, and has good thermodynamic stability, yield and solubility. A most preferred germline light chain is O12, preferably the rearranged germline kappa light chain IgVκ1-39*01/IGJκ1*01 (nomenclature according to the IMGT database found on the web at imgt.org) or fragment or a functional derivative thereof. Such single VL is also referred to as common VL, or common light chain. Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. A "common light chain" according to the invention refers to light chains which may be identical or have some amino acid sequence differences while retaining the binding specificity of the antibody. It is for instance possible within the scope of the definition of common light chains as used herein, to prepare or find light chains that are not identical but still functionally equivalent, e.g. by introducing and testing conservative amino acid changes, changes of amino acids in regions that do not or only partly contribute to binding specificity when paired with the heavy chain, and the like. It is an aspect of the present invention to use as single VL one identical light chain that can combine with different heavy chains to form antibodies with functional antigen binding domains (WO2004/009618, WO2009/157771, Merchant et al., 1998, Nissim et al., 1994).

The terms 'amplification of nucleic acid sequences encoding immunoglobulin heavy chain variable regions' and '(at least partially) sequencing of nucleic acids' have their usual meanings in the art.

The term 'frequency analysis' has its usual meaning in the art. For a more detailed explanation of the term, see e.g. example 1 of the present invention.

The term 'desired VH sequences' means those VH sequences that, based on the frequency analysis, are produced in response to exposure to an antigen. These are assumed to encode VH regions that are specific for said antigen. Typically, an immune response to an antigen in a mouse entails the activation of about 100 different B cell clones (Poulsen et al., J Immunol 2011; 187; 4229-4235). Therefore, it is most preferred to select the 100 most abundant clones. More practically, at least 20, preferably about 50 abundant clones are selected.

'Host cells' according to the invention may be any host cell capable of expressing recombinant DNA molecules, including bacteria, yeast, plant cells, eukaryotes with a preference for mammalian cells. Particularly when larger antibody formats are desired bacterial cells are not suitable and mammalian cells are preferred. Suitable mammalian host cells for expression of antibody molecules are known in the art.

It is an aspect of the invention to provide a method according to the invention as described above, further comprising taking a sample of said cultured cells, the sample comprising at least one of said binding molecules, and subjecting the samples to at least one functional assay, and selecting at least one cell that expresses a binding molecule with desired characteristics.

A 'functional assay' as used herein means a test to establish properties such as binding specificity, affinity, neutralizing activity, tumor cell killing, proliferation inhibition or any other desired functional characteristic or activity of the binding molecule produced according to the methods of the invention. Such assays are used to determine early on whether binding molecules obtained are suitable for the desired purpose. Said desired purpose may be a diagnostic and/or therapeutic application. In one embodiment of the invention, the method for producing a defined population of binding molecules further comprises the step of harvesting the supernatants of the cultured cells, the supernatants containing said binding molecules, and subjecting the supernatants to at least one functional assay. Irrespective of a functional assay as described above, the present invention also compasses ways to determine the identity of the binding molecules, using methods known in the art.

It is an aspect of the invention to provide a method according to the invention as described above, further comprising providing said host cell with means for expression of said at least one VH and VL in a desired format. The term 'desired formats' as used herein refers to a form of the binding molecule in which it can be used for its particular purpose. The typical formats of binding molecules, in particular antibody like molecules that are suitable for particular purposes are well known in the art. For therapy these molecules would typically be fully human monoclonals (mono- or bispecific, and/or mixtures thereof, i.e.) Oligoclonics®. For imaging these molecules would typically be antibody fragments, and so on. Desired formats include, but are not limited to, bispecific formats such as DARTS™, BiTEs™, single light chain bispecific antibodies (Merchant et al., 1998) including CH3-engineered bispecifics such as knob-into-hole variants or charge-engineered CH3 variants, DVD-Ig antibodies (Wu et al., 2007), mixtures of antibodies (de Kruif et al., 2009) and the like.

In a further preferred embodiment, the population of B cells that is provided for the method for producing a defined population of binding molecules is enriched for B cells that express immunoglobulin receptors that bind to the antigen. Such enrichment may occur when a B cell encounters antigen (e.g. when a mouse is immunized with an antigen) and is activated to divide to generate a clone of B cells. It is an object of the present invention to provide a method for producing a population of defined binding molecules further providing B cell clones wherein said collection of B cell clones comprise a collection of VH regions that are enriched for VH regions encoding antibodies directed to the antigen or epitope of interest. Such enrichment can, for example, be carried out by taking only those B cell clones obtained from antigen-exposed animals as a starting population that are selected through an antigen recognition process, i.e. by using selection methods comprising coated or labeled antigen. Typically, the 20 most abundant clones, preferably, the 50 most abundant clones, more preferably the 100 most abundant clones are selected; most preferably, the 200 most abundant clones are selected.

In a preferred embodiment, the antigen-specific VH regions are clonally related. In another preferred embodiment, the population of B cells is highly-enriched for B cells that express immunoglobulin receptors that bind to the antigen. In this case, the majority of B cells that are provided will be antigen specific, and thus, an amplification step of all nucleic acid sequences encoding VH regions may not be necessary and all isolated nucleic acids from said B cells can be, at least partially, sequenced directly. It is thus an aspect of the present invention, to provide for a method for producing a defined population of binding molecules, said method comprising at least the step of providing a population of B cells expressing a limited VL repertoire wherein said B cells comprise a collection of VH regions that is enriched for VH regions encoding antibodies directed to the antigen or epitope of interest.

It is an aspect of the invention to provide a method according to the invention, wherein said population of B cells is obtained from a transgenic mouse carrying a limited, preferably human, VL repertoire.

It is an aspect of the invention to provide a method according to the invention, wherein said mouse has been immunized such that selective clonal expansion of B cells that react with the antigen or epitope of interest is preferentially induced.

An 'immunization protocol that causes the selective expansion of B cells' as used herein means that primary and booster immunizations are designed to cause selective expansions of B cells that produce antibodies that bind to the antigen or epitope of interest. The immunization protocol may for example use different forms or fragments of the antigen during primary immunization and each subsequent booster immunization. For example, the antigen may be expressed on the membrane of a cell, a recombinant protein, a recombinant protein fused to another protein, a domain of a protein or a peptide of a protein. The immunization protocol may include the use of an adjuvant during the primary and/or booster immunizations. In a preferred embodiment, an adjuvant is used during primary immunization only to limit the extent of non-specific expansion of bystander B cells. Bystander B cells are cells that are activated without the step of binding of antigen to the antibody receptor expressed on the surface of the B cell. It is known in the art that immunization with Fc-fusion proteins for example, often results in a robust anti-Fc response where up to about 70% of all B cells react to the Fc part of the fusion protein rather than to the antigen of interest. In the most preferred embodiment, an immunization protocol is used without adjuvant to preferentially expand B cells that have been activated by the antigen used for immunization. It is therefore an aspect of the invention to provide a method for producing a defined population of binding molecules, said method comprising at least the step of providing a population of B cells expressing a limited VL repertoire, wherein said population of B cells is obtained from a transgenic mouse carrying a limited, preferably human, VL repertoire, wherein said mouse has been immunized with an antigen, such that selective clonal expansion of B cells that react with the antigen or epitope of interest is preferentially induced. A preferred way of inducing selective clonal expansion of B cells is DNA tattoo vaccination. The term 'DNA tattoo vaccination' refers to an invasive procedure involving a solid vibrating needle loaded with plasmid DNA that repeatedly punctures the skin, wounding both the epidermis and the upper dermis and causing cutaneous inflammation followed by healing (Bins 2005/Pokorna 2008).

In transgenic mice with human antibody genes, a plurality of human IgH V regions and/or a plurality of human Ig light chain kappa V regions have been introduced in the genome of the animals (Lonberg 2005). Upon immunization, these mice mount an antigen-specific immune response that is diversified in heavy and light chain V region utilization. It is anticipated that, upon immunization of these transgenic mice with antigen, high throughput sequencing, frequency ranking of VH and VL genes, construction of CDR3 heat maps and random or frequency-guided pairing of VH and VL regions yields a large proportion of antibodies that do not bind to the antigen or bind with low affinity (Reddy et al., 2010). It is therefore an object of the present invention to use transgenic animals that harbor a restricted repertoire of human immunoglobulin light chains for immunization purposes. Such transgenic animals that harbor a limited repertoire of human light chains are described in WO2009/157771. Preferably, the endogenous kappa light chain is functionally silenced in such animals to minimize the use of murine light chains in antibodies generated in such mice. In a further embodiment, also the endogenous lambda light chain is functionally silenced to further reduce the use of murine light chains in antibodies. In a most preferred embodiment, transgenic animals that carry a single rearranged human VL region that is resistant to somatic hypermutation is used for immunization to generate antibodies in which the processes of somatic mutation and clonal expansion and selection mainly act on the VH regions of the antibody expressed on the membrane of a B cell. Hence, high throughput sequencing and creation of CDR3 heat maps to identify antigen-driven, clonally expanded B cells and the antibodies they encode may focus on VH regions only. It is therefore an aspect of the present invention to provide a method for producing a defined population of binding molecules, said method comprising the step of providing a population of B cells, wherein said population of B cells is obtained from a transgenic animal, preferably a mouse, carrying a limited, preferably human, VL repertoire, wherein said animal has been immunized with an antigen. In a preferred embodiment, the invention provides for a method for producing a defined population of binding molecules, said method comprising the step of providing a population of B cells, wherein said population of B cells is obtained from a transgenic mouse carrying a single rearranged human VL, preferably the human IGVκ1-39 light chain (WO2009/157771). The advantage of this germline human IGVκ1-39 light chain is its anticipated reduced immunogenicity due to absence of strong non-self DRB1 binders (WO2009/157771, example 19). In addition, this light chain is known to be capable of pairing with many different human VH regions. Through an array of genetic mechanisms, the antibody VL repertoire that can be generated in an animal is virtually unlimited.

In one aspect according to the invention, the method for producing a defined population of binding molecules further comprises the step of providing the host cell with means for expression of the at least one VH and VL in a desired format. The term 'desired format' as used herein means that the selected VH and VL sequences are expressed together with other sequences such that antibody formats can be expressed within the host cell. In one embodiment, after selection of suitable VHs, mixtures of antibodies are produced by a single cell by introducing at least 2 different heavy chains and one common light chain into a cell (WO2004/009618). In another embodiment, after selection of suitable VH regions, the at least two different heavy chains are engineered such that heterodimerization of heavy chains is favored over homodimerization. Alternatively, the engineering is such that homodimerization is favored over heterodimerization. Examples of such engineered heavy chains are for example the protuberance and cavity (knob-into-hole) constructs as described in WO98/050431, or the charge-variants as described (Gunasekaran et al., 2010) or WO2009/089004, or WO2006/106905.

It is another aspect of the invention to provide a method for producing a defined population of binding molecules, wherein said binding molecules have a desired effect according to a functional screening assay, the method further comprising the step of taking the supernatants of said cultured cells, the supernatants comprising said binding molecules, subjecting the supernatants to at least one functional screening assay, and selecting at least one cell that expresses a binding molecule with desired characteristics. Preferably, said host cell comprises a nucleic acid sequence encoding a common light chain that is capable of pairing with said desired VH, such that produced antibodies comprise common light chains, as described above. In specific embodiments said culturing step and said screening step of the method is performed with at least two clones. The method may optionally include an assay for measuring the expression levels of the antibodies that are produced. Such assays are well known to the person skilled in the art, and include protein concentration assays, immunoglobulin specific assays such as ELISA, RIA, and the like.

The present invention inter alia describes a method for producing a defined population of binding molecules, wherein the starting point is a population of B cells that expresses a restricted repertoire of light chain variable (VL) regions and a diversified repertoire of heavy chain variable regions (VH). The VL region repertoire may for example be restricted by limiting the number of V and J genes available during recombination in a transgenic animal or by inserting one or a few pre-rearranged VL regions in the genome of a transgenic animal, by reducing or abrogating the rate of somatic mutation occurring in the VL region or by a combination of these strategies (WO2009/157771). The VH regions may be diversified by recombination of V, D and J gene segments and somatic mutation. Upon immunization, collections of heavy chain nucleic acid sequences are obtained from B cells in the lymphoid organs of transgenic animals, subjected to high throughput sequencing and analyzed to rank all unique heavy chains based on frequency and to rank HCDR3 based on length, percentage identity and frequency to construct HCDR3 heat maps. Nucleotide sequence information is used to rank VH regions according to their frequency in the collection and frequently occurring sequences, assumingly representing VH regions expressed in B cells that have undergone clonal expansion as a result of antigen stimulation, are cloned into expression vectors in conjunction with one of the VL regions present in the restricted repertoire. By using a restricted VL repertoire, the search for original VH/VL pairs is highly simplified because no VL sequence information needs to be retrieved, analyzed or ranked from the immunized animal; in case the original restricted VL repertoire comprises a single VL, all VH/VL combinations will represent original pairs as used by B cells in vivo. In case the original restricted VL repertoire contained a few VL regions, combination with the ranked VH regions yields only small collections of VH/VL combinations that can be rapidly screened for binding and functional activity.

Expression vectors containing the VH and VL regions are used to transfect cells to rapidly obtain antibodies for binding assays and functional screening. Different formats of antibodies can be obtained by using expression vectors that contain different genetic elements that, for example, drive the formation of antibody fragments or antibodies with different isotypes, bispecific antibodies, mixtures of antibodies or antibodies that have engineered variable or constant regions for modified effector functions or modified half life, or contain additional binding sites, are devoid of amino acid sequences that have a deleterious effect on development, production or formulation of antibodies such as glycoslylation and deamidation sites.

EXAMPLES

Example 1

Deep Sequence Analysis and Frequency Ranking of VH Genes Expressed in Murine Spleen B Cells Using VH Family-Specific Primers This example describes the use of high throughput sequencing to retrieve and analyze the repertoire of antibody VH regions expressed in the spleen of wild type mice immunized with the antigens ErbB2 or ErbB3. Because immunization will enrich the B cell population for clones directed against the immunogen, it is anticipated that sequencing large numbers of VH transcripts identifies these B cell clones as they will be present within the population in higher frequencies. In this example, approximately 25,000 VH region genes from the spleen of a single immunized mouse are retrieved by high throughput sequencing and ranked based on frequency.

Spleens were collected from mice immunized with either the antigen ErbB2 or ErbB3 using DNA tattooing (see example 6). A single cell suspension was prepared according to standard techniques. B cells were isolated from this splenic single cell suspension in a two-step MACS procedure using materials from Miltenyi biotec (http://www.miltenyibiotec.com/en/default.aspx). Briefly, splenic B cells were isolated by first depleting the non-B cells, followed by positive selection of B cells. The non-B cells were depleted by labeling of T cells, NK cells, myeloid cells, plasma cells and erythrocytes with a cocktail of biotinylated antibodies (Table 1) and subsequent incubation with streptavidin Microbeads. Next the non-B cells were depleted over an LD column. The flow through, containing the enriched B cell fraction, was labeled with magnetic Microbeads using FITC conjugated anti-IgG1 and IgG2ab antibodies (Table 1) followed by labeling with anti-FITC Microbeads (Miltenyi Biotec, Cat no. 130-048-701). The IgG labeled cells were subsequently positively selected over an LS column (Miltenyi Biotec, Cat no 130-042-401). MACS procedures were performed according to Kit/Microbead specific manuals supplied by Miltenyi. The purity of the isolated B cells was determined by FACS analysis according to standard techniques using the antibodies listed in Table 2.

TABLE 1 antibodies to label non-B cells

| Ab # | Antigen | Label | Clone | Supplier | Cat no. |
|---|---|---|---|---|---|
| Ab0064 | IgG1 | FITC | A85-1 | Becton Dickinson | 553443 |
| Ab0131 | IgG2ab | FITC | R2-40 | Becton Dickinson | 553399 |
| Ab0158 | CD138 | Biotin | 281-2 | Becton Dickinson | 553713 |
| Ab0160 | CD3E | Biotin | 145-2C11 | eBioscience | 13-0031 |
| Ab0161 | Ly-6G | Biotin | RB6-8C5 | eBioscience | 13-5921 |
| Ab0162 | TER-119 | Biotin | TER-119 | eBioscience | 13-5921 |
| Ab0163 | CD49b | Biotin | DX5 | eBioscience | 13-5971 |
| Ab0164 | CD11b | Biotin | M1/70 | eBioscience | 13-0112 |

TABLE 2 antibodies for FACS analysis

| Ab # | Antigen | Label | Clone | Supplier | Cat no. |
|---|---|---|---|---|---|
| Ab0064 | IgG1 | FITC | A85-1 | Becton Dickinson | 553443 |
| Ab0131 | IgG2ab | FITC | R2-40 | Becton Dickinson | 553399 |
| Ab0067 | CD138 | APC | 281-2 | Becton Dickinson | 558626 |
| Ab0160 | IgM | PE-CY7 | II/41 | eBioscience | 25579082 |
| Ab0161 | IgD | PE | 11-26 | eBioscience | 12599382 |
| Ab0162 | CD19 | PerCP-cy5.5 | 1D3 | eBioscience | 45019382 |
| Ab0163 | B220 | Aallphycocyaninefluor 780 | RA3-6B2 | eBioscience | 47045282 |

To extract the nucleic acids of the B cells, cells were lysed in Trizol LS (Invitrogen), RNA was prepared and cDNA synthesized according to standard techniques. Primers designed for amplification of murine VH repertoires were taken as starting material and were modified for use in 454 high throughput sequencing by addition of 454 primer sequences (forward 454 primer: CGTATCGCCTC-CCTCGCGCCATCAG (SEQ ID NO: 1); reverse 454 primer: CTATGCGCCTTGCCAGCCCGCTCAG (SEQ ID NO: 2)). The complete primer sequences for the PCR amplification of murine VH repertoires are shown in Tables 3 and 4.

TABLE 3

The forward 454 Phusion primers, complete. The phusion part (CGTATCGCCTCCCTCGCGCCATCAG) (SEQ ID NO: 1) is in italic, in bold is the 5'part of the VH genes.

| Name | sequence | SEQ ID NO: | wobble |
|---|---|---|---|
| mIGHV1A_454 | *CGTATCGCCTCCCTCGCGCCATCAG*__GAGKTCMAGCTGCAGCAGTC__ | 3 | K = 15% T/85% G  M = 15% A/85% C |
| mIGHV1B_454 | *CGTATCGCCTCCCTCGCGCCATCAG*__SAGRTCCASCTGCAGCAGTC__ | 4 | S1 = 5% G/95% C  R = 95% A/95% G<br>S2 = 95% G/5% C |
| mIGHV1C_454 | *CGTATCGCCTCCCTCGCGCCATCAG*__SAGGTCCAGCTHCAGCAGTC__ | 5 | S = 50% C/50% G  H = 33% A/33% C/33% T |
| mIGHV1D_454 | *CGTATCGCCTCCCTCGCGCCATCAG*__SAGRTCCAGCTGCAACAGTC__ | 6 | S = 80% G/20% C  R = 15% A/85% G |
| mIGHV1E_454 | *CGTATCGCCTCCCTCGCGCCATCAG*__CAKGTCCAACTGCAGCAGCC__ | 7 | K = 15% T/85% G |
| mIGHV1F_454 | *CGTATCGCCTCCCTCGCGCCATCAG*__CAGGCTTATCTACAGCAGTC__ | 8 | |
| mIGHV1G_454 | *CGTATCGCCTCCCTCGCGCCATCAG*__CAGCGTGAGCTGCAGCAGTC__ | 9 | |
| mIGHV2_454 | *CGTATCGCCTCCCTCGCGCCATCAG*__CAGGTGCAGMTGAAGSAGTC__ | 10 | M = 15% A/85% C  S = 50% C/50% G |

TABLE 3-continued

The forward 454 Phusion primers, complete. The phusion part
(CGTATCGCCTCCCTCGCGCCATCAG) (SEQ ID NO: 1) is in italic, in bold is the 5'part of the VH genes.

| Name | sequence | SEQ ID NO: | wobble |
|---|---|---|---|
| m1GHV3_454 | *CGTATCGCCTCCCTCGCGCCATCAG*SAKRTGCAGCTTCAGGAGTC | 11 | S = 80% G/20% C  K = 50% G/50% T<br>R = 15% A/85% G |
| m1GHV4_454 | *CGTATCGCCTCCCTCGCGCCATCAG*GAGGTGAAGCTTCTCCAGTC | 12 | |
| mIGHV5A_454 | *CGTATCGCCTCCCTCGCGCCATCAG*GAAGTGMWGCTGGTGGAGTC | 13 | M = 15% A/85% C  W = 80% A/20% T |
| mIGHV5B_454 | *CGTATCGCCTCCCTCGCGCCATCAG*GAVGTGAAGCTSGTGGAGTC | 14 | V = 20% C/40% G/40% A  S = 80% G/20% C |
| mIGHV6A_454 | *CGTATCGCCTCCCTCGCGCCATCAG*GAAGTGAARMTTGAGGAGTC | 15 | R = 50% A/50% G  M = 50% A/50% C |
| mIGHV6B_454 | *CGTATCGCCTCCCTCGCGCCATCAG*GATGTGAACCTGGAAGTGTC | 16 | |
| mIGHV6C_454 | *CGTATCGCCTCCCTCGCGCCATCAG*GAGGAGAAGCTGGATGAGTC | 17 | |
| mIGHV7_454 | *CGTATCGCCTCCCTCGCGCCATCAG*GAGGTGMAGCTGRTGGAATC | 18 | M = 50% A/50% C  R = 50% A/50% G |
| mIGHV8_454 | *CGTATCGCCTCCCTCGCGCCATCAG*CAGRTTACTCWGAAASAGTC | 19 | R = 50% A/50% G  W = 20% A/80% T<br>S = 80% G/20% C |
| mIGHV9_454 | *CGTATCGCCTCCCTCGCGCCATCAG*CAGATCCAGTTSGTRCAGTC | 20 | S = 80% G/20% C  R = 15% A/85% G |
| mIGHV10_454 | *CGTATCGCCTCCCTCGCGCCATCAG*GAGGTGCAGCTTGTTGAGTC | 21 | |
| mIGHV11_454 | *CGTATCGCCTCCCTCGCGCCATCAG*GAAGTGCAGCTGTTGGAGAC | 22 | |
| mIGHV13_454 | *CGTATCGCCTCCCTCGCGCCATCAG*SAGGTGCAGCTKGTAGAGAC | 23 | S = 50% C/50% G  K = 50% G/50% T |
| mIGHV15_454 | *CGTATCGCCTCCCTCGCGCCATCAG*CAGGTTCACCTACAACAGTC | 24 | |

TABLE 4

The reverse 454 Phusion primers, complete. The phusion part
(CTATGCGCCTTGCCAGCCCGCTCAG) (SEQ ID NO: 2) is in italic. The
part specific for the murine J segments are in bold.

| Name | sequence | SEQ ID NO: |
|---|---|---|
| mIGHJ1_454 | *CTATGCGCCTTGCCAGCCCGCTCAG*GAGGAGACGGTGACCGTGGTCCC | 25 |
| mIGHJ2b_454 | *CTATGCGCCTTGCCAGCCCGCTCAG*GAGGAGACTGTGAGAGTGGTGCC | 26 |
| mIGHJ3_454 | *CTATGCGCCTTGCCAGCCCGCTCAG*GCAGAGACAGTGACCAGAGTCCC | 27 |
| mIGHJ4b_454 | *CTATGCGCCTTGCCAGCCCGCTCAG*GAGGAGACGGTGACTGAGGTTCC | 28 |

In the PCR, the four reverse JH primers were mixed in equal ratios prior to use. The forward primers were not mixed, so 22 PCR reactions were performed. The PCR reaction products were analyzed on gel and it was expected to yield PCR products of 350 to 400 base pairs in length. Some PCR products were mixed based on frequency of VH genes in normal repertoires (Table 5, below). The intensities of the bands on gel were expected to correspond to the ratios listed in this table and when this was the case, PCR products were mixed for sequencing based on volumes. Where intensities of bands on gel did not correspond to ratios listed in Table 5, over- or under represented bands could be adjusted. As high throughput sequencing also identifies the primer and the PCR reaction, ratios can always be 'adjusted' after sequencing and the frequency of each VH gene per PCR reaction analyzed.

TABLE 5

| PCR products that can be pooled. | |
|---|---|
| Pool name | Percentage (%) |
| 1A | 39 |
| 1B | |
| 1CD | |
| 1EFG | |
| 2 | 4 |
| 3/4 | 7 |
| 5 | 15 |
| 6 | 1 |
| 7/8 | 10 |
| 9 | 16 |
| 10/11 | 6 |
| 13/15 | 2 |

Sequence analysis was performed in order to rank all unique VH genes from a single animal, immunization, and/or cell population on frequency:

- Raw sequences were analyzed to identify those that encode a VH region open reading frame that at least contains HCDR3 plus some neighboring framework sequence to identify the VH. Preferably, the VH region open reading frame contains CDR1 to framework 4
- All sequences were translated into amino acid sequences
- All sequences were clustered based on identical HCDR3 protein sequence
- All clusters were ranked based on number of VH sequences in each cluster
- An alignment of all sequences in each cluster was made based op protein sequences, in which differences with the germline VH and germline JH are indicated. All identical sequences in the alignment are again clustered.

This provides information on the most frequently occurring VH gene within a CDR3 cluster. This gene may have differences compared to the germline as a result of somatic hypermutation. This gene is chosen for construction and expression with the common VL gene High throughput sequencing was performed using Roche 454 sequencing on samples from an individual immunized mouse. Other high throughput sequencing methods are available to a skilled person and are also suitable for application in the method. In total, 118,546 sequence reads were used as a raw data set to first identify sequences that represented full length VH regions or portions thereof encoding at least 75 amino acids. For each sequence within this set, frameworks 2-4 and all 3 CDR regions were identified as described (Al-Lazikani et. al., 1997). Sequences were subsequently subjected to a number of criteria including the presence of a canonical cysteine residue, the absence of stop codons and the minimal length for each CDR regions. All VH regions fulfilling these criteria were then clustered to identify the frequency in which each unique CDR3 are used, thereby generating heavy chain CDR3 heat maps. Then, all identical clones in each CDR3 cluster were grouped and aligned with the germ line VH sequence. This analysis allows for the identification of abundantly used VH genes in large repertoires.

Albeit that this analysis can be carried out manually, the use of an algorithm including the above instructions greatly facilitates the analysis process (Reddy et al., 2010)

A total of 18,659 clusters were identified within 30,995 annotated VH sequences and 2,733 clusters were found that had more than 1 member. In addition, 123 clusters had more than 20 members. The first 40 clusters of these are shown in Table 6. Nine clusters had more than 100 members. The number of 30.000 sequences is more than sufficient as many clones appear only once and the experiments are aimed at identifying frequent clones. In fact, less than 30.000 sequences would work quite well. Alignments of the two largest clusters demonstrated the presence of 100% germline genes and variants containing mutations throughout the VH gene (data not shown).

TABLE 6

Example of clusters identified by unique CDR3.

| cluster # | # identical sequences | HCDR3 | SEQ ID NO: |
|---|---|---|---|
| Cluster001 | 337 | YSNYWYFDV | 29 |
| Cluster002 | 212 | GGLRGYFDV | 30 |
| Cluster003 | 130 | YDSNYWYFDV | 31 |

TABLE 6-continued

Example of clusters identified by unique CDR3.

| cluster # | # identical sequences | HCDR3 | SEQ ID NO: |
|---|---|---|---|
| Cluster004 | 124 | TYDNYGGWFAY | 32 |
| Cluster005 | 116 | AGLLGRWYFDV | 33 |
| Cluster006 | 116 | RDY | |
| Cluster007 | 113 | RFGFPY | 34 |
| Cluster008 | 103 | AITTVVATDY | 35 |
| Cluster009 | 102 | AYYYGGDY | 36 |
| Cluster010 | 99 | SGPYYSIRYFDV | 37 |
| Cluster011 | 91 | SEGSSNWYFDV | 38 |
| Cluster012 | 89 | GTLRWYFDV | 39 |
| Cluster013 | 76 | DFYGSSYWYFDV | 40 |
| Cluster014 | 75 | DNWDWYFDV | 41 |
| Cluster015 | 73 | FYDYALYFDV | 42 |
| Cluster016 | 72 | GNYGSSYFDY | 43 |
| Cluster017 | 72 | WKVDYFDY | 44 |
| Cluster018 | 70 | GGYWYFDV | 45 |
| Cluster019 | 69 | YKSNYWYFDV | 46 |
| Cluster020 | 66 | LLPYWYFDV | 47 |
| Cluster021 | 64 | SYYGSSYWYFDV | 48 |
| Cluster022 | 63 | GGYYGSRDFDY | 49 |
| Cluster023 | 63 | DYDWYFDV | 50 |
| Cluster024 | 61 | TYNNYGGWFAY | 51 |
| Cluster025 | 57 | GGLYYDYPFAY | 52 |
| Cluster026 | 57 | WGDYDDPFDY | 53 |
| Cluster027 | 56 | DYYGSSYWYFDV | 54 |
| Cluster028 | 55 | EATY | 55 |
| Cluster029 | 52 | YGSSYWYFDV | 56 |
| Cluster030 | 52 | WGYGSKDAMDY | 57 |
| Cluster031 | 51 | WGRELGNYFDY | 58 |
| Cluster032 | 49 | YGNYWYFDV | 59 |
| Cluster033 | 48 | TVTTGIYYAMDY | 60 |
| Cluster034 | 48 | HYYSNYVWWYFDV | 61 |
| Cluster035 | 47 | GALRGYFDV | 62 |
| Cluster036 | 47 | HYYGSTWFAY | 63 |
| Cluster037 | 45 | LGAYGNFDY | 64 |
| Cluster038 | 44 | REFAY | 65 |
| Cluster039 | 43 | EAAYYFDY | 66 |
| Cluster040 | 43 | GSLRGYFDV | 67 |

Example 2

Deep Sequence Analysis and Frequency Ranking of VH Genes Expressed in Murine IgG+ Spleen B Cells Using a Single Primer Set In this example, a primer specific for the IgG CH1 constant region was used to interrogate the repertoire of VH gene sequences expressed in IgG+ memory B cells in the spleen of mice immunized with the ErbB2-Fc fusion protein. At the 5' end of the mRNA an oligonucleotide primer was annealed to a triple guanine stretch that was added to each mRNA by an MMLV reverse transcriptase. This 5' primer introduces a priming site at the 5'end of all cDNAs. Using this approach, amplifications of all VH regions expressed in IgG+ B cells can be done using the 5' primer and the CH1 primer, preventing a potential bias introduced by the use of a large number of VH family-specific primers and focusing the analysis on a population of B cells that has apparently undergone activation and isotype switching as a result of stimulation with antigen.

Wild-type C57BL/6 mice were immunized intraperitoneally with ErbB2-Fc protein (1129ER, R&D systems) dissolved in Titermax Gold adjuvant (TMG, Sigma Aldrich, T2684) on days 0, 14, and 28 and with ErbB2-Fc in PBS at day 42. Total splenic B cells were purified on day 45 by MACS procedure as detailed in Example 1. The total splenic B cell fraction from successfully-immunized mice, as determined by serum antibody titers in ELISA, contained 5-10% IgG+ B cells. This material was used to optimize the PCR conditions.

Transgenic mice containing the human HuVκ1-39 light chain, as described in (WO2009/157771) were either immunized with EGFR-Fc fusion protein (R&D Systems, Cat no 334-ER) emulsified in Titermax Gold adjuvant (TMG, Sigma Aldrich, T2684) or, as a control, with Titermax Gold adjuvant emulsified with PBS at an interval of 14 days. The latter group was included to identify the VH repertoire of B cells responding to the adjuvant alone. Mice were three times immunized with EGFR-Fc/adjuvant emulsion or adjuvant emulsion alone on days 0, 14 and 28. At day 35 the anti-EGFR serum titer was determined by FACS using standard procedures. Mice that had developed at day 35 a serum titer>1/1.000 received a final intraperitoneal boost with EGFR-Fc protein dissolved in PBS at day 42 followed by collection of spleen at day 45 for isolation of splenic B cells. Splenic B cells were isolated from the total spleen by positive selection using mouse CD19-specific magnetic beads. The splenic B cell fraction was lysed in Trizol LS to isolate total RNA.

After RNA isolation cDNA was prepared (cell populations from HuVκ1-39 light chain transgenic mice and mock and control/test sample with similar cell population) using MMLV reverse transcriptase in the presence of primers mouse CH1 rev 0, 1, 2 or 3 together with MMLV 454 fw (Table 7). Four different primers were tested to identify the one that resulted in optimal cDNA yields and PCR products; MMLV was designed to contain the 3' GGG stretch similar to the Clontech primers, deleting cloning sites but adding 454 sequences (SMARTer™ RACE cDNA Amplification Kit, Cat#634924, Clontech).

As a control, cDNA was also prepared using the standard Clontech protocol; the SMARTer PCR cDNA synthesis kit using the SMARTer II A oligo together with the gene specific CH1 rev 0, 1, 2 or 3 primers (SMARTer™ RACE cDNA Amplification Kit, Cat#634924, Clontech). Using standard procedures, the optimal PCR cycle number and optimal primer combination were determined. The Clontech protocol was followed for PCR conditions.

Next, material from immunized HuVκ1-39 light chain transgenic mice and mock-immunized mice was amplified under optimal conditions. Preferably amplifications were carried out with a reverse primer upstream from the primer used in cDNA synthesis to obtain a more specific PCR product (nested PCR). cDNA was cloned in pJET according to the manufacturer's instructions (CloneJET PCR cloning kit, Fermentas #K1232) and Sanger-sequence 100 clones. PCR product of material derived from the immunized and mock-immunized animals was purified and used for 454 sequencing. The data were analyzed and used to construct CDR3 heat maps are constructed as described in example 1.

TABLE 7

Figure 1:
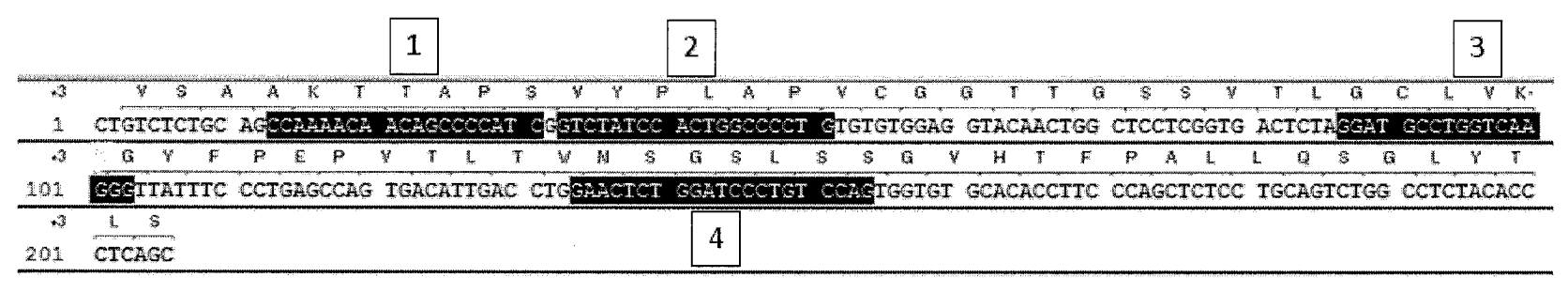

Primers used in this study. Primer MMLV 454 fw hybridizes at the 5'end of the mRNA. The position of the CH1 rev primers is indicated in FIG. 1.

| number | Name | Sequence | SEQ ID NO: |
| --- | --- | --- | --- |
| DO_1165 | MMLV 454 fw | *CGTATCGCCTCCCTCGCGCCATCAG*GGG | 68 |
| DO_1166 | 454 fw | *CGTATCGCCTCCCTCGCGCCATCAG* | 1 |
| DO_1167 | mouse CH1 rev 0 | TGATGGGGGTGTTGTTTTGG | 69 |
| DO_1168 | mouse CH1 rev 1 | CAGGGGCCAGTGGATAGAC | 70 |
| DO_1169 | mouse CH1 rev 2 | GCCCTTGACCAGGCATCC | 71 |
| DO_1170 | mouse CH1 rev 3 | CTGGACAGGGATCCAGAGTTC | 72 |
| DO_1171 | mouse CH1 454 rev 0 | *CTATGCGCCTTGCCAGCCCGCTCAG*TGATGGGGGTGTTGTTTTGG | 73 |
| DO_1172 | mouse CH1 454 rev 1 | *CTATGCGCCTTGCCAGCCCGCTCAG*CAGGGGCCAGTGGATAGAC | 74 |
| DO_1173 | mouse CH1 454 rev 2 | *CTATGCGCCTTGCCAGCCCGCTCAG*GCCCTTGACCAGGCATCC | 75 |
| DO_1174 | mouse CH1 454 rev 3 | *CTATGCGCCTTGCCAGCCCGCTCAG*CTGGACAGGGATCCAGAGTTC | 76 |
| DO_1175 | smart IV oligo | AAGCAGTGGTATCAACGCAGAGTGGCCATTACGGCCGGG | 77 |

TABLE 7-continued

Primers used in this study. Primer MMLV 454 fw hybridizes at the 5'end of the mRNA. The position of the CH1 rev primers is indicated in FIG. 1.

| number | Name | Sequence | SEQ ID NO: |
|---|---|---|---|
| DO_1176 | smart IV oligo short | AAGCAGTGGTATCAACGCAGAGTGGG | 78 |
| DO_1177 | 5PCR primer 454 | *CGTATCGCCTCCCTCGCGCCATCAG*AAGCAGTGGTATCAACGCAGAGT | 79 |

Legends:
454 5' sequence *CGTATCGCCTCCCTCGCGCCATCAG* (SEQ ID NO: 1)
454 3' sequence *CTATGCGCCTTGCCAGCCCGCTCAG* (SEQ ID NO: 2)
SMART sequence AAGCAGTGGTATCAACGCAGAGT (SEQ ID NO: 80)
SfiI GGCCATTACGGCC (SEQ ID NO: 81)

The results of these experiments yield heavy chain CDR3 heat maps that represent sequences used by B cells that have undergone activation and isotype switching as a result of stimulation by antigen. The VH region sequences present in the most frequently-occurring clusters derived from the transgenic mice containing the human IGVκ1-39 light chain can be used to combine with the sequence of human IGVκ1-39 light chain to collections of human monoclonal antibodies enriched for antibodies specific for EGFR.

Example 3

Deep Sequence Analysis and Frequency Ranking of VH Genes Expressed in Murine IgG+ Spleen B Cells without VH Family Specific Primers For this example, the objective was to optimize deep sequencing technology of IgG VH genes by using amplifications based on primers that amplify all Ig heavy chains and thus to prevent potential bias introduced by VH family specific primers.

Antibody VH gene amplification for phage display library generation uses primers that append restriction sites for cloning to VH genes at the required position within the genes. This requires primer annealing sites within the VH genes and therefore VH family specific primers. In example 1 such primer sequences were used. A downside of the use of VH family primers is that they amplify a subset of all VH genes in the repertoire. As a large collection of primers and PCR reactions is used to amplify all genes and the PCR products are mixed afterwards, this will result in skewing of the ratios of the VH genes originally present in the samples and therefore over/under representation of VH genes in the final sequenced repertoire. To circumvent these problems in this study the RACE (Rapid Amplification of cDNA Ends) amplification protocol was used in combination with an IgG1-CH1 specific primer set. The SMARTer RACE kit (Clontech; cat #634923 & #634924) was used which couples a 5' synthetic adaptor to the mRNA. The SMARTScribe RT enzyme produces a copy of the RNA transcript. The SMARTScribe RT starts the cDNA synthesis from the IgG mRNA at an antisense primer that recognizes a known sequence in the IgG mRNA such as the poly A tail in this study. When the SMARTScribe RT enzyme reaches the 5'end of the IgG RNA template it adds 3 to 5 residues to the 3' end of the first-strand cDNA. The SMARTer oligo IIA contains a terminal stretch of modified bases that anneals to this extended tail added by the SMARTScribe RT, allowing the oligo to serve as a template for the RT. Subsequently the SMARTScribe RT switches templates from the mRNA molecule to the SMARTer oligo IIA, generating a complete double strand cDNA copy of the original RNA with the additional SMARTer sequence at the end. Thereafter, for PCR amplification of VH cDNA, an oligo that anneals to the 5' SMART sequence on one end of the cDNA (5 PCRprimer 454) and an IgG-CH1 specific primer at the other end of the cDNA are applied (Table 8). In this way the VH regions from IgG heavy chains are amplified with just one primer combination, independent from VH family specific primers, and in this case a primer specific for the IgG CH1 constant region was used to interrogate the repertoire of VH gene sequences expressed in IgG+ memory B cells in the spleen of mice immunized with the ErbB2-Fc fusion protein. In the best case the IgG-CH1 specific reverse primer should anneal as close as possible to the VH gene to increase the chance that the full VH gene can be sequenced.

Samples for deep sequencing were obtained from two immunized transgenic mice carrying the human huVk1-39 light chain; mice were numbered mouse 1145 and mouse 1146. Briefly, transgenic mice containing the human HuVκ1-39 light chain, as described in (WO2009/157771) were immunized with EGFR-Fc fusion protein (R&D Systems, Cat no 334-ER) emulsified in Titermax Gold adjuvant (TMG, Sigma Aldrich, T2684). Mice were three times immunized with EGFR-Fc/adjuvant emulsion on days 0, 14 and 28. At day 35 the anti-EGFR serum titer was determined by FACS using standard procedures. Mice that had developed at day 35 a serum titer>1/1.000 received a final intraperitoneal boost with EGFR-Fc protein dissolved in PBS at day 42 followed by collection of spleen at day 45 for isolation of splenic B cells. Splenic B cells were isolated from the total spleen by positive selection using mouse CD19-specific magnetic beads. The splenic B cell fraction was lysed in Trizol LS to isolate total RNA according to standard procedures.

cDNA was synthesized from these RNA samples using the SMARTer RACE cDNA Amplification kit according to manufacturer's instructions to come to so-called RACE-Ready cDNA. This RACE-ready cDNA was subsequently amplified by PCR according to manufacturer's instructions and the SMART specific primer (Table 8) and one of several IgG CH1 specific primers were used to establish which IgG-CH1 specific primer amplifies the IgG transcript best. The IgG-CH1 specific reverse primers DO_1171 to DO_1174 containing the 3' 454 sequences were tested and as a forward primer the SMART tag specific primer containing the 5' Roche 454 sequencing tag (DO_1177) was used (see table 8 and FIG. 1) (SMARTer™ RACE cDNA Amplification Kit, Cat#634923&634924, Clontech). The PCR schedule used is shown in Table 9.

TABLE 8

Primers used in this study. The position of the CH1 rev primers is indicated in FIG. 1.

| number | Name | Sequence | SEQ ID NO: |
|---|---|---|---|
| DO_1171 | mouse CH1 454 rev 0 | *CTATGCGCCTTGCCAGCCCGCTCAG*TGATGGGGGTGTTGTTTTGG | 73 |
| DO_1172 | mouse CH1 454 rev 1 | *CTATGCGCCTTGCCAGCCCGCTCAG*CAGGGGCCAGTGGATAGAC | 74 |
| DO_1173 | mouse CH1 454 rev 2 | *CTATGCGCCTTGCCAGCCCGCTCAG*GCCCTTGACCAGGCATCC | 75 |
| DO_1174 | mouse CH1 454 rev 3 | *CTATGCGCCTTGCCAGCCCGCTCAG*CTGGACAGGGATCCAGAGTTC | 76 |
| DO_1177 | 5PCR primer 454 | *CGTATCGCCTCCCTCGCGCCATCAG*AAGCAGTGGTATCAACGCAGAGT | 79 |

Legends:
454 5' sequence *CGTATCGCCTCCCTCGCGCCATCAG* (SEQ ID NO: 1)
454 3' sequence *CTATGCGCCTTGCCAGCCCGCTCAG* (SEQ ID NO: 2)
SMART sequence AAGCAGTGGTATCAACGCAGAGT (SEQ ID NO: 80)

TABLE 9

PCR schedule.

| Step | Temperature | Time | Number of cycles |
|---|---|---|---|
| 1 | 98° C. | 30 seconds | 1 |
| 2 | 98° C. | 25 seconds | 10 |
| 3 | 72° C.-54° C. | 25 seconds | Touchdown |
| 4 | 72° C. | 50 seconds | |
| 5 | 98° C. | 25 seconds | 14 |
| 6 | 58° C. | 25 seconds | |
| 8 | 72° C. | 50 seconds | |
| 9 | 72° C. | 3 minutes | 1 |
| 10 | 16° C. | ∞ | |

PCR results are shown in FIG. 2 demonstrating that DO_1171 did not give a PCR product, whereas the other three all gave an abundant PCR product, see FIG. 2. It was concluded that DO_1172 is the best option to amplify the VH region, since this primer is closest to the VH gene and produces in PCR a clear and specific band.

The PCR was performed several times on template (Table 9) to obtain enough material (500-1000 ng) for deep sequencing. To determine the DNA concentration after PCR, a fluorimetric quantification of DNA was performed. In this case, Quant-IT Picogreen dsDNA (Invitrogen P7589) measurements were performed using a Biotek Synergy. PCR product of material derived from the immunized animals (samples 1145 and 1146) was subsequently sent to Eurofins MWG Operon (found on the web at eurofinsdna.com) for high throughput sequencing.

Eurofins first ligated barcoded linkers to each of the two samples. In this way both samples could be sequenced in one chip-segment, thereby reducing costs. With this layout Eurofins provided sequencing with GS FLX+ technology where length read is 600-700 bp on average.

Deep sequencing revealed more than 50.000 reads per mouse and data were analyzed as explained in example 1. Table 10 provides the 25 largest clusters from two of the analyzed samples.

TABLE 10

Cluster size, HCDR3 sequence and VH genes used are presented from cDNA samples from mouse 1145 and 1146. #/25 provides the frequency of the VH gene in 25 clusters.

| sample 1145 Cluster Name | Cluster Size | CDR3 sequence | SEQ ID NO: | VH gene | #/25 |
|---|---|---|---|---|---|
| Cluster001 | 1243 | HYSDYPYFDY | 82 | J558.66.165 | 19 |
| Cluster002 | 858 | YGDYINNVDY | 83 | J558.66.165 | |
| Cluster003 | 543 | GFYGYDF | 84 | 7183.19.36 | 1 |
| Cluster004 | 376 | LDTIVEDWYLDV | 85 | J558.66.165 | |
| Cluster005 | 335 | LDTVVEDWYFDV | 86 | J558.66.165 | |
| Cluster006 | 320 | YGDYSNYVDY | 87 | J558.66.165 | |
| Cluster007 | 313 | TRQFRLRDFDY | 88 | J558.83.189 | 1 |
| Cluster008 | 290 | FDYGSTQDYAMDY | 89 | J558.66.165 | |
| Cluster009 | 213 | SGNYDFYPMDY | 90 | J558.66.165 | |
| Cluster010 | 205 | RLVEY | 91 | J558.66.166 | 1 |
| Cluster011 | 197 | YGDYSNNVDY | 92 | J558.66.165 | |
| Cluster012 | 194 | LDDGYPWFAY | 93 | J558.55.149 | 1 |
| Cluster013 | 182 | LSDYGSSAYLYLDV | 94 | J558.66.165 | |

TABLE 10-continued

Cluster size, HCDR3 sequence and VH genes used are presented from cDNA samples from mouse 1145 and 1146. #/25 provides the frequency of the VH gene in 25 clusters.

| Name | Size | CDR3 | SEQ ID NO: | VH | #/25 |
|---|---|---|---|---|---|
| Cluster014 | 180 | QVDYYGSSYWYFDV | 95 | J558.66.165 | |
| Cluster015 | 179 | LGYGSSYLYFDV | 96 | J558.66.165 | |
| Cluster016 | 175 | LGYGSIYLYFDV | 97 | J558.66.165 | |
| Cluster017 | 168 | LTDYGSGTYWFFDV | 98 | J558.66.165 | |
| Cluster018 | 162 | LDYYGSSYGWYFDV | 99 | J558.66.165 | |
| Cluster019 | 162 | YGDYINSVDY | 100 | J558.66.165 | |
| Cluster020 | 159 | YTDYINSVDY | 101 | J558.66.165 | |
| Cluster021 | 156 | LDTIVEDWYFDV | 102 | J558.66.165 | |
| Cluster022 | 148 | DYYGSSYGFDY | 103 | VGAM66.165 | 1 |
| Cluster023 | 147 | IYSNSLIMDY | 104 | J558.66.165 | |
| Cluster024 | 143 | LGYGSSYWYFDV | 105 | J558.66.165 | |
| Cluster025 | 142 | GGYYPYAMDY | 106 | J558.12.102 | 1 |
| Total | 7190 | | | # different VH | 7 |

| sample 1146 Name | Size | CDR3 | SEQ ID NO: | VH | #/25 |
|---|---|---|---|---|---|
| Cluster001 | 2570 | EGRGNYPFDY | 107 | 36-60.6.70 | 2 |
| Cluster002 | 1791 | DYSYYAMDY | 108 | J559.12.162 | 1 |
| Cluster003 | 1251 | MRLYYGIDSSYWYFDV | 109 | 3609.7.153 | 3 |
| Cluster004 | 905 | MRLFYGSRYSYWYFDV | 110 | 3609.7.153 | |
| Cluster005 | 841 | SYYYGSRESDY | 111 | J558.53.146 | 1 |
| Cluster006 | 614 | GKYYPYYFDY | 112 | J558.12.102 | 2 |
| Cluster007 | 515 | WGSSGY | 113 | J558.55.149 | 1 |
| Cluster008 | 477 | TGYNNYGSRFIY | 114 | J558.18.108 | 3 |
| Cluster009 | 441 | RLVDY | 115 | J558.67.166 | 3 |
| Cluster010 | 378 | WWFLRGVYVMDY | 116 | J558.85.191 | 4 |
| Cluster011 | 306 | TGYNNYGSRFTY | 117 | J558.18.108 | |
| Cluster012 | 303 | RLVEY | 91 | J558.67.166 | |
| Cluster013 | 291 | RLIEY | 118 | J558.67.166 | |
| Cluster014 | 291 | GDWYFDV | 119 | VGAM.8-3-61 | 2 |
| Cluster015 | 265 | RQFLLGVYAMDY | 120 | J558.85.191 | |
| Cluster016 | 237 | RHFLLGVYAMDY | 121 | J558.85.191 | |
| Cluster017 | 230 | EGRVTTLDY | 122 | 36-60.6.70 | |
| Cluster018 | 216 | GDWYFDY | 123 | VGAM.8-3-61 | |
| Cluster019 | 212 | MRLFYGSSYSYWYFDV | 124 | 3609.7.153 | |
| Cluster020 | 203 | GSGYVYAMDY | 125 | VGAM3.8-4-71 | 1 |
| Cluster021 | 200 | GTTAYYAMDY | 126 | VGAM3.8-3-61 | 2 |
| Cluster022 | 197 | TGYNNYGSRFAY | 127 | J558.18.108 | |

TABLE 10-continued

Cluster size, HCDR3 sequence and VH genes used are
presented from cDNA samples from mouse 1145 and
1146. #/25 provides the frequency of the VH gene
in 25 clusters.

| Cluster023 | 182 | GKYYPYYFVY | 128 | J558.12.102 |
|---|---|---|---|---|
| CIuster024 | 163 | GTTAYYAMDY | 129 | VGAM3.8-3-61 |
| Cluster025 | 153 | RGSYGTCFDY | 130 | J558.85.191 |
| Total | 13232 | | | # different VH 12 |

The results from Table 10 show that different VH genes were amplified and sequenced in the PCR and deep sequencing procedures. Sample 1145 contains many clusters within the 25 largest clusters that use the J558.66.165 gene. Sample 1146 contains a large diversity of VH genes with 12 different VH genes in which each is present between one and four times within the 25 largest clusters. These results suggest that the method allows unbiased amplification and analysis of IgG VH repertoires.

To conclude, these experiments resulted in a ranking of the most frequent VHs that represent sequences used by B cells that have undergone activation and isotype switching as a result of stimulation by antigen. The VH region sequences present in the most frequently-occurring clusters derived from the transgenic mice containing the human IGVκ1-39 light chain can be used to combine with the sequence of human IGVκ1-39 light chain to collections of human monoclonal antibodies enriched for antibodies specific for EGFR.

Example 4

Immunization Strategies for the Construction of Reliable VH CDR3 Heat Maps

A broad array of Immunization methods is available that use various formats of antigen in combination with adjuvant to optimize the antigen-specific immune response in animals. For the ranking of frequently used heavy chain genes optimally representing VH regions from B cells that have expanded as a result of stimulation with the antigen of interest, it is critical that immunization protocols are used that focus the immune response on said antigen or even on an epitope of said antigen. Thus, the use of antigens fused or coupled to carrier proteins (such as Fc fusion proteins or proteins coupled to carriers like Keyhole Limpet Hemocyanine, known in the art) is to be avoided or restricted to a single step in the immunization procedure like a single primary immunization or a single booster immunization. It is expected that even limited activation of B cells through the use of carrier or fusion proteins or adjuvant may show up in ranked VH sequences/HCDR3 heat maps, thereby contaminating the analysis. Ideally, the immunizations are thus performed with 'essentially pure antigens'. The present example demonstrates that single or repeated immunization with an antigen fused to an Fc-portion indeed results in expansion of irrelevant B cells, i.e. B cells that react with the Fc-portion rather than with the antigen of interest.

Single human VL transgenic mice (group 1) and wildtype mice (group 2) were immunized with the EGFR overexpressing tumor cell line A431 on days 0 and day 14 (2×10E6 A431 cells in 200 µl PBS), followed by ip immunization with Fc-EGFR fusion protein emulsified in Titermax Gold. At day 35, serum was collected and tested in ELISA for the presence of anti-Fc antibodies.

As control, a third group of mice comprising both single human VL transgenic mice and wildtype mice (group 3) were immunized with Fc-EGFR fusion protein only on days 0, 14, 28, 42 and 52. At day 56, serum was collected and tested in ELISA for the presence of anti-Fc antibodies.

Figure 3:
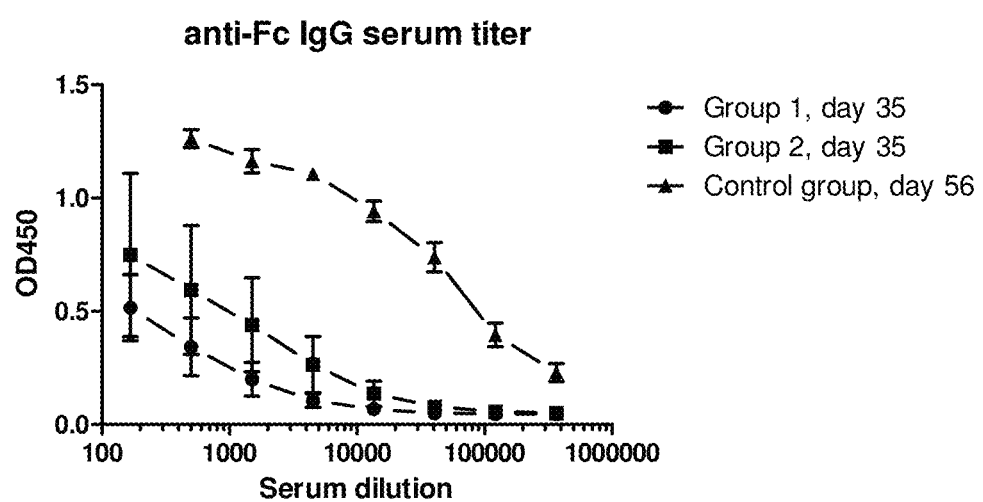
FIG. 3 is a graph showing the by-stander immune response against Fc portion of Fc-EGFR fusion protein upon immunization.

The results (FIG. 3) show that even after a single immunization with Fc-EGFR, antibodies against the Fc portion are detected in groups 1 and 2. Although the levels of anti-Fc antibodies in these two groups were lower than the levels of anti-Fc as observed in group 3, the VH regions encoding these anti-Fc antibodies will be found in CDR3 heat maps, constructed as described in example 1. If so desired, such Fc-specific binders can either be circumvented by using essentially pure antigens such as in DNA tattoo or by elimination of Fc-specific binders from the population of B cells prior to VH sequence analysis.

Example 5

DNA Vaccination by Tattooing

DNA vaccination exploits plasmid DNA encoding a protein antigen to induce an immune response against said protein antigen. There is no need for purification of proteins for immunization and proteins, including membrane proteins, are expressed in their natural configuration on a cell membrane (Jechlinger et al., 2006/Quaak, et al., 2008/Stevenson et al., 2004).

In this example, we have used DNA tattoo vaccination, an invasive procedure involving a solid vibrating needle loaded with plasmid DNA that repeatedly punctures the skin, wounding both the epidermis and the upper dermis and causing cutaneous inflammation followed by healing (Bins 2005/Pokorna 2008). Here we used DNA tattoo vaccination strategies to induce antibody responses in mice. The goal was to assess the quality of the antibody response in the absence or presence of adjuvant. As described in example 4, for the construction of adequate CDR3 heat maps, it is desirable to focus the antibody response on the antigen of interest, omitting the use of adjuvant that causes clonal expansion of unwanted B cells.

For tattoo vaccination, plasmids encoding human ErbB2 and plasmids encoding influenza virus Hemagglutinin (HA) were used. Three DNA tattoo vaccination strategies were tested to optimize the priming and boosting of the immune response: (A) vaccination with vector DNA encoding the ErbB2 or HA antigen, (B) vaccination of vector DNA encoding ErbB2 or HA together with an adjuvant or (C) heterologous prime-boost vaccination with DNA encoding ERbB2 or HA followed by a boost with purified ErbB2 or HA protein in TM Gold adjuvant. In addition, control group (group D) mice were immunized with purified ErbB2 or HA in TM Gold adjuvant. To establish an optimized DNA tattoo vaccination protocol the following immunization protocols were used:

Group A (DNA Only):

In this group, mice were vaccinated on day 0, 3, and 6 with plasmid DNA encoding ErbB2 or HA in the absence of adjuvant followed by a boost with the same DNA after four weeks. No adjuvant was used.

Group B (DNA+ Genetic Adjuvant):

To test if an adjuvant increases the priming of the humoral immune response, plasmid DNA encoding TANK-binding kinase 1 (TBK1) was co-vaccinated with ErbB2 or HA plasmid DNA. It has been shown that TBK1 acts as an adjuvant for DNA vaccination using a gene gun (Ishii et al., 2009). Comparison of group B with group A will reveal what impact the genetic adjuvant has on the generation of antibodies specific for HA or ErB2. Animals in group B were DNA vaccinated at same time points as those in group A. To examine the contribution of genetic adjuvant in priming of the immune system, plasmid DNA encoding TBK-1 was mixed in a 1:1 ratio with pVAX1-ErbB2 or pVAXI-HA and subsequently administrated by DNA tattoo. To this end mice are vaccinated with 20 μg pTBK-1 and 20 μg pVAX1-ErbB2 or pVAX1-HA in 10 μl PBS.

Group C (DNA+ Protein):

In this group a heterologous prime-boost protocol with DNA tattoo followed by intraperitoneal (i.p.) protein boost was tested to examine if a final protein boost is required to induce an antigen-specific serum IgG titer of >1/1000 and if this boost is necessary to efficiently induce splenic memory B cells. I.p. injection is the direct immunization route to the spleen. So, by first priming the immune system by DNA vaccination ErbB2 or HA is presented to the immune system as in vivo expressed protein. Subsequently, the primed immune system was boosted with ErbB2 or HA in adjuvant via the i.p. injection route to induce a systemic immune reaction. Comparison of group C to A reveals the impact of the systemic boost on 1) antigen-specific IgG serum titer and 2) on generation of the splenic memory B cell compartment.

Immunization and first boost with pVAXI-ErbB2 or pVAX1-HA were carried out according to the scheme described for group A. Subsequently mice are boosted at day 28 and day 42 with 20 μg of protein in 200 μl emulsion of TitermaxGold adjuvant or in 200 μl PBS, respectively, administrated via ip injection. For HA vaccination mice were injected with 20 μg HA (Meridian life Science Inc, Cat no R01249). For ErbB2 mice were injected with 20 μg of a truncated ErbB2 protein: the extra cellular domain (ECD, aa23-652) of ErbB2 fused to FC-tail (R&D systems, Cat no 1129ER).

Group D (Protein):

In this control group mice were vaccinated i.p. with ErbB2 or HA in adjuvant. Material from this group served as positive control for the analyses of the samples from groups A-C. At day 0, 14 and 28 mice were vaccinated with 20 μg of ErbB2 or HA in 200 μl emulsion of TitermaxGold adjuvant. For final boost, mice received 20 μg of ErbB2 or HA dissolved in 200 μl PBS.

Serum titer and affinity were determined after each boost by ELISA and FACS respectively using standard protocols (Middendorp et al., 2002). To study affinity maturation during the vaccination protocol, the relative affinity of the polyclonal antigen-specific-IgG serum was determined by ELISA. The efficacy and quality of memory B cell induction at the end of each vaccination strategy was examined by FACS in spleen and draining inguinal lymph node (iLN) as described (Middendorp et al., 2002).

All ErbB2 DNA immunized mice developed an anti-ErbB2 IgG serum titer>10,000 after two immunization rounds (FIG. 4A-C), indicating that two rounds of DNA immunization via tattoo are sufficient to induce a strong anti-ErbB2 antibody response. The results show protein immunized mice develop a strong anti-ERbB2 IgG serum titer at day 21 (FIG. 4D).

Figure 4:
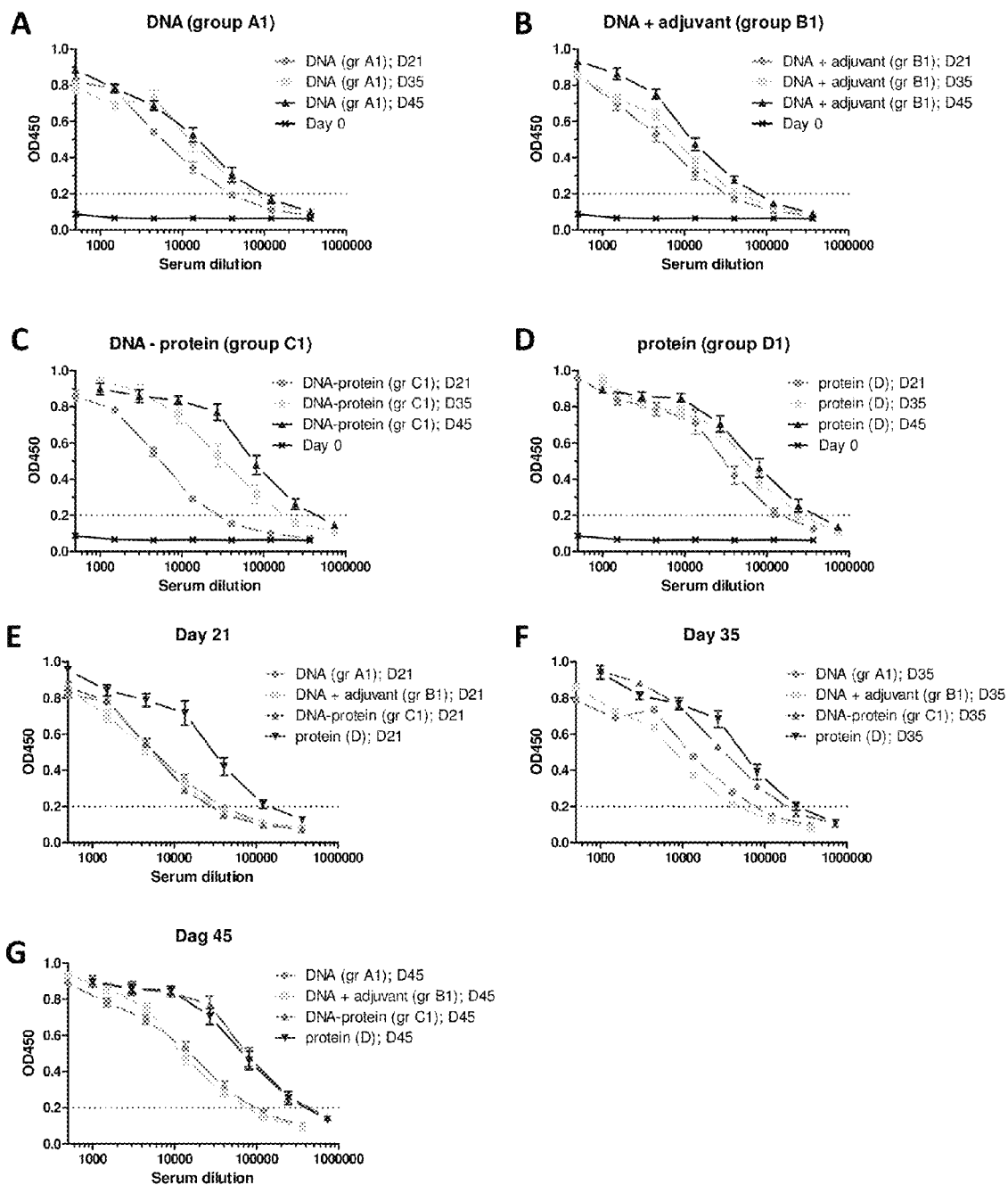
FIG. 4 depicts the ErbB2 specific IgG serum titer in ErbB2 vaccinated mice.

A third immunization round at day 28 with DNA (groups A1 and B1) resulted in a further increase of the anti-ErbB2 IgG serum titer at day 35 (seven days after third vaccination round) and day 45 (end point) (FIGS. 4A and 3B). In group B1 we found that co-administration of the ErbB2 expression vector (group A1) together with a DNA-adjuvant (the pBoost3 vector encoding the TBK1 protein), would boost the antibody response against ErbB2. Comparison of the anti-ErbB2 serum titer in time showed that the mice in the groups A1 and B1 developed a comparable anti-ErbB2 serum titer (FIG. 4E-G). This indicated that for the ErbB2 antigen co-administration of the pBoost3 vector failed to enhance the polyclonal anti-ErbB2 IgG serum titer. The mice in group C1 first received two immunization rounds (day 0 and 14) with DNA followed by a boost (at day 28) with ErbB2-Fc protein emulsified with TitermaxGold adjuvant. This protein boost at day 28 resulted in a strong increase of the anti-ErbB2 IgG serum titer at day 35 (after third immunization at day 28) and day 45 (end point) (FIG. 4C). At day 35 the serum titer of group C1 (DNA-protein) was higher compared to the DNA only vaccinated mice (groups A1 and B1) and marginal lower compared to protein only immunized mice (group D1). At day 45 the serum titers of the groups C1 (DNA and protein) and D1 (protein only) were comparable.

Figure 5:
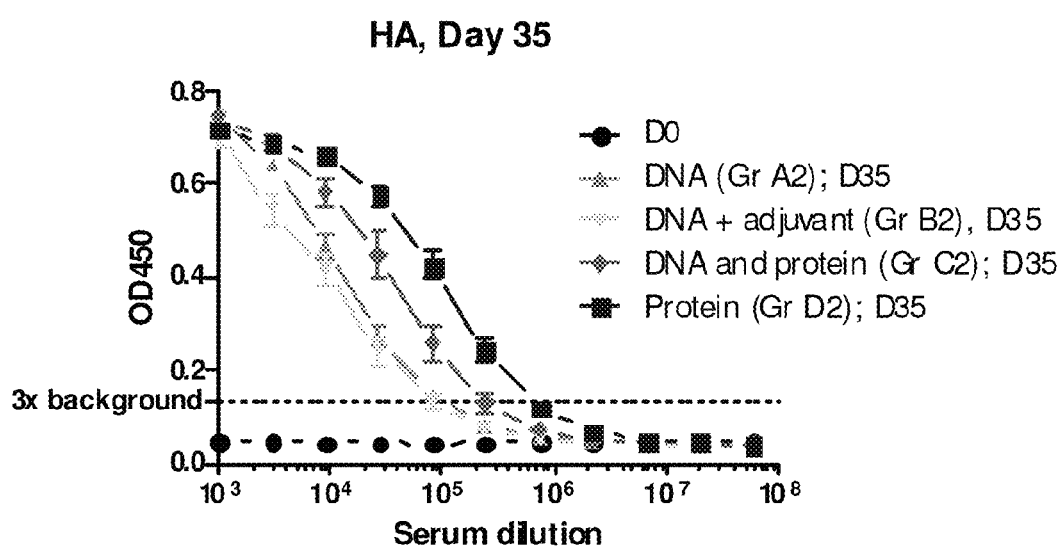
FIG. 5 depicts the HA specific IgG serum titer in HA vaccinated mice.

All mice that were immunized with the HA antigen via the four vaccination strategies developed a strong anti-HA IgG serum titer at day 21 (data not shown) and 35 (FIG. 5). The anti-HA IgG serum titer between the DNA (group A2) and DNA+ adjuvant (group B2) strategies were comparable. Moreover, DNA vaccination followed by a boost with HA protein emulsified with Titermax Gold (group C2) or three times immunization with protein (group 02) gave higher serum titer than DNA only vaccination. In summary, the similarities and differences between the four mice groups vaccinated with HA antigen were comparable to the results observed for the ErbB2 vaccinated mice in terms of antigen specific IgG serum titer.

To further compare the vaccination strategies we compared the polyclonal anti-ErbB2 IgG serum based on relative affinity. The relative affinity was measured in day 45 sera samples, obtained three days after the final boost. The relative affinity was determined by ELISA by incubating at a fixed serum dilution on an ErbB2 antigen titration starting at 0.5 μg/ml. The selected fixed serum dilution was based on the serum dilution at which the sera reached the plateau using a fixed concentration of ErbB2 antigen in ELISA (0.5 μg/ml). The fixed serum dilution was 1:1,500 for groups A1 and B1, and 1:20,000 for the groups C1 and D1. To compare the individual groups we calculated and plotted the relative binding based on the reduction of absorbance versus the antigen dilution range. For each antigen concentration we calculated the relative binding, the OD of 0.5 μg/ml was set to 100%.

Figure 6:
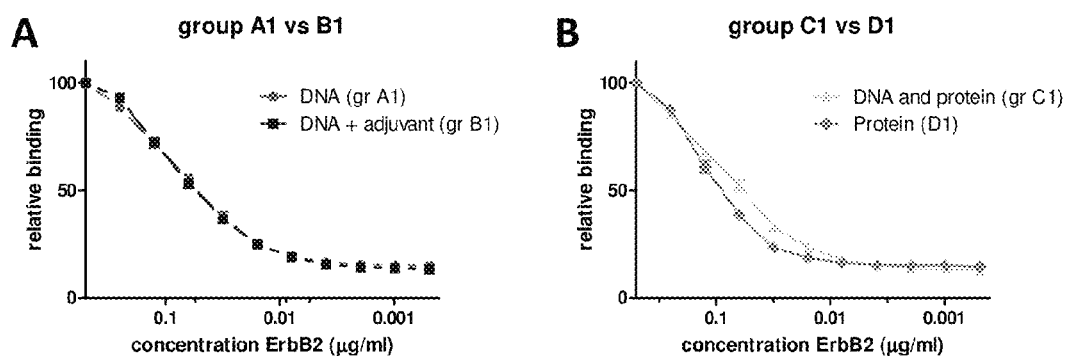
FIG. 6 depicts the relative affinity of the anti-ErbB2 IgG polyclonal sera of ErbB2 vaccinated mice as determined by ELISA.

First we compared DNA vaccination with (group B1) and without DNA adjuvant (group A1) (FIG. 6A). No difference was observed in the relative binding between the groups that received DNA (group A1) or DNA+ adjuvant (group B1). This indicated that the DNA adjuvant did not enhance the affinity of the polyclonal serum. In addition, to compare the contribution of priming of the immune response with DNA followed by a protein boost we compared the sera of DNA-protein (group C1) and protein (group D1) (FIG. 6B). The relative binding was significant higher for group C1 than for group D1 (p<0.001 at antigen concentrations 0.0625 and 0.0313 µg/ml). This suggested that the relative affinity of the polyclonal serum was on average higher for mice in group C1 than for mice in group D1.

Isolation and analysis of tissues from immunized mice: Total splenic and total inguinal lymph node fractions from ErbB2 and HA vaccinated mice were collected and saved in Trizol LS. The draining inguinal lymph node from the tattooed leg was isolated and saved in Trizol LS.

In addition we enriched the splenic IgG B cell fraction by MACS from mice immunized using strategy C1 and C2. Finally we determined the fraction of splenic IgG+ B cells in all ErbB2 and HA vaccinated mice. To isolate the splenic IgG+ B cells we performed a two step MACS purification. In the first step we depleted the non-B cell using biotinylated non-B cell specific antibodies. In the second step we enriched the splenic IgG B cells using anti-IgG1 and anti-IgG2ab specific antibodies. Table 11 gives an overview from which mice the splenic IgG (IgG1 and IgG2ab) B cells were isolated. Purity of the isolated IgG fractions was determined by FACS using B cell specific and IgG1/IgG2ab specific antibodies. The % Ig B cells was determined by staining a fraction of cells alter the depletion step. Table 11 summarizes the yield and purity of the isolated IgG+ B cell fractions per mouse and antigen used for immunization.

TABLE 11 yield and purity of the isolated IgG+ B cell fractions

| Strategy and experimental group | Antigen | Animal number | % B cells/total life gate | % IgG B cells/B cell gate | Total IgG cells (E+0.6) |
|---|---|---|---|---|---|
| DNA and protein | ErbB2 | 31 | 68.46 | 30.27 | 1.36 |
| DNA and protein | ErbB2 | 32 | 67.37 | 39.96 | 1.76 |
| DNA and protein | ErbB2 | 33 | 20.78 | 61.75 | 3.63 |
| DNA and protein | ErbB2 | 34 | 72.97 | 73.67 | 1.17 |
| DNA and protein | ErbB2 | 35 | 86.67 | 77.34 | ND |
| DNA and protein | ErbB2 | 36 | 84.98 | 82.12 | ND |
| DNA and protein | ErbB2 | 37 | 85.03 | 74.32 | ND |
| DNA and protein | HA | 38 | 90.41 | 55.48 | 2.09 |
| DNA and protein | HA | 40 | 92.60 | 49.09 | 1.17 |
| DNA and protein | HA | 41 | 86.03 | 47.02 | 0.84 |
| DNA and protein | HA | 42 | 88.46 | 46.99 | 1.21 |

To examine what protocol gives the best induction of the memory B cell compartment, we examined the size of IgG B cell compartment in the spleen and the iLN per each vaccination strategy by FACS. We used a cocktail of anti-IgG1-FITC and anti-IgG2ab-FITC monoclonals to visualize the IgG B cell fraction. Table 12 gives an overview of the percentages B cells within the lymphocyte gate and the percentages IgG B cells within the B cell fraction per mouse and tissue.

TABLE 12

IgG+ B cell fraction in the spleen and lymph node of ErbB2 vaccinated mice

| Group | Animal number | Spleen % B cells/ lympho. gate | Spleen % IgG+ B cells/ lympho. gate | iLN % B cells/ lympho. gate | iLN % IgG+ B cells/ lympho. gate |
|---|---|---|---|---|---|
| DNA (A1) | 1 | 57.50 | 1.27 | 58.26 | 1.86 |
| DNA (A1) | 2 | 51.81 | 1.09 | 51.09 | 2.80 |
| DNA (A1) | 3 | 54.05 | 1.32 | 58.93 | 2.43 |
| DNA (A1) | 4 | 54.06 | 1.73 | 55.24 | 2.93 |
| DNA (A1) | 5 | 54.93 | 2.72 | 53.78 | 6.45 |
| DNA (A1) | 6 | 58.68 | 1.98 | 53.89 | 2.90 |
| DNA (A1) | 7 | 56.46 | 5.92 | 52.01 | 10.74 |
| DNA + Adju (B1) | 17 | 49.05 | 4.33 | 51.04 | 7.02 |
| DNA + Adju (B1) | 17 | 55.84 | 1.55 | 53.80 | 4.38 |
| DNA + Adju (B1) | 18 | 44.13 | 4.05 | 54.78 | 6.31 |
| DNA + Adju (B1) | 19 | 34.99 | 5.56 | 53.39 | 15.47 |
| DNA + Adju (B1) | 20 | 51.81 | 1.41 | 60.30 | 2.40 |
| DNA + Adju (B1) | 21 | 54.13 | 1.21 | 56.35 | 2.84 |
| DNA + Adju (B1) | 22 | 58.34 | 2.11 | 62.29 | 1.80 |
| DNA + protein (C1) | 31 | 48.99 | 6.26 | 54.12 | 6.49 |
| DNA + protein (C1) | 32 | 49.76 | 7.38 | 51.79 | 7.67 |
| DNA + protein (C1) | 33 | 45.94 | 12.76 | 45.14 | 4.19 |
| DNA + protein (C1) | 34 | 30.50 | 16.07 | 44.83 | 10.91 |
| DNA + protein (C1) | 35 | 43.48 | 26.62 | 44.60 | 8.16 |

TABLE 12-continued

IgG+ B cell fraction in the spleen and lymph node of ErbB2 vaccinated mice

| | | Spleen | | iLN | |
|---|---|---|---|---|---|
| Group | Animal number | % B cells/ lympho. gate | % IgG+ B cells/ lympho. gate | % B cells/ lympho. gate | % IgG+ B cells/ lympho. gate |
| DNA + protein (C1) | 36 | 41.12 | 24.07 | 45.13 | 11.00 |
| DNA + protein (C1) | 37 | 30.50 | 21.10 | 30.82 | 9.17 |

Figure 7:
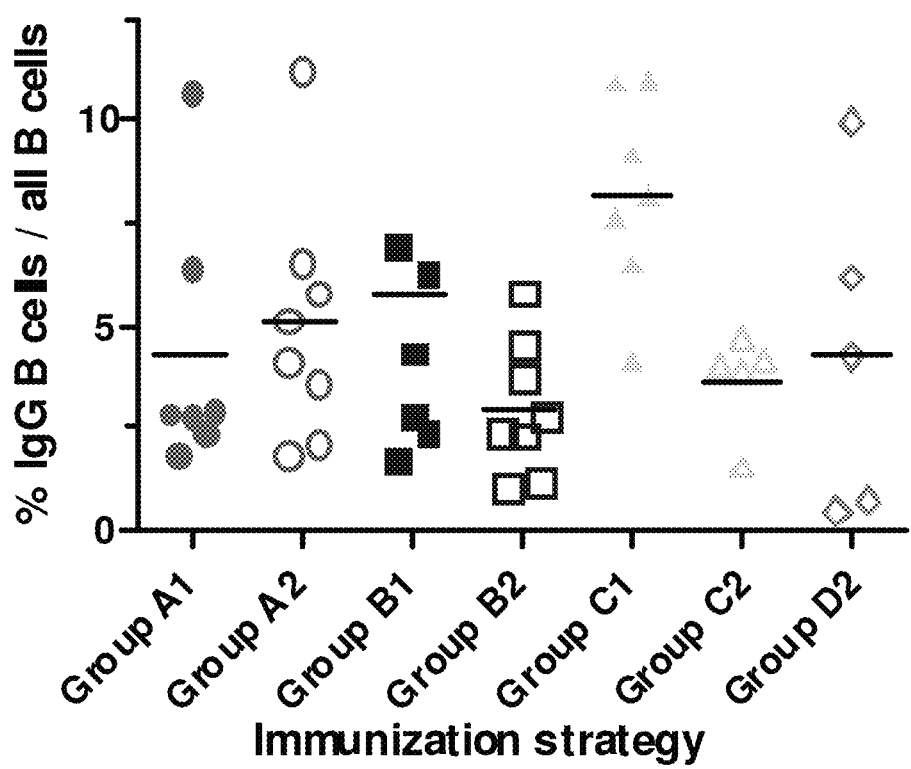
FIG. 7 is a graph showing the comparison of the percentages IgG B cells per total iLN B cells per vaccination strategy and per antigen.

The mice from group C1 (DNA-protein) that received a correct i.p. boost with ErbB2-Fc protein at day 28 (mice 35-37) had the largest fraction of IgG+ B cells per splenic B cell population. This was expected as i.p. injection is the direct route of the antigen to the spleen. The percentages of IgG+ B cells in the iLN of group A1 (DNA) and B1 (DNA+ adjuvant) ranged between 1.8-15.47 with an averaged IgG+ B cell fraction of 4.3 and 5.7 for group A1 or B1, respectively. Interestingly, the mice from group A1 and B1 with the highest fraction of IgG+ B cells in the iLN also contained a higher percentage of splenic IgG+ B cells. Analysis of the percentages of IgG B cells in the iLN of the HA vaccinated mice showed that these mice had on average comparable percentages of IgG+ B cells per all iLN B cells as found in the A1 and B1 groups. The averaged percentages of IgG+ B cells in the iLN of DNA vaccinated (group A2) and the DNA+ adjuvant vaccinated (group B2) mice was 5.0 and 3.0, respectively. FIG. 7 gives a comparison of the percentages IgG B cells/iLN B cells per vaccination strategy and per antigen. In summary, these data showed that the draining iLN of DNA only (group A) of DNA+ adjuvant (group B) vaccinated mice had a significant fraction of IgG+ B cells. Mice that received a protein boost (group C) contained a larger IgG+ B cell population in spleen and iLN.

We conclude that mice that were vaccinated with DNA or vaccinated with DNA and boosted with protein developed a strong antigen specific IgG serum titer. The relative affinity of the sera against ErbB2 can be significantly enhanced using a DNA+ protein immunization protocol instead of a protein immunization protocol. The small variation of the antigen IgG serum titer between individual DNA vaccinated mice shows that the DNA tattoo method has been carried out consistently. DNA vaccination with ERbB2 and HA both resulted in strong antigen specific antibody response.

It was reported that the adjuvant effect of plasmid DNA is mediated by its double-stranded structure, which activates Tbkl-dependent innate immune signaling pathways in the absence of HRs (Ishii et al., 2008). Therefore, co-administration of a Tbkl-expressing plasmid was expected to further boost DNA vaccine-induced immunogenicity. In our setting, we did not observe a beneficial effect of the co-administration of the Tbkl encoding pBoost3 vector. Co-administration of pBoost3 together with the antigen encoding vector failed to result in a higher serum titer, increased relative affinity or enhanced IgG B cell formation.

FACS analysis showed that the draining iIN in a mouse vaccinated with only DNA (group A and B) contains a significant IgG+ B cell fraction. However the number of IgG B cells that can be isolated from a single draining iIN is very limited due to the size of an iIN. Moreover, the fraction of IgG+ B cells in the iLN varied significantly between individual DNA vaccinated mice. This could be the results of variation in administration of DNA via DNA tattoo. Interestingly, the mice with a high percentage of iIN IgG+ B cells also had a higher percentage of splenic IgG+ B cells. Another strategy to obtain a larger number of IgG+ B cells is to boost the DNA vaccinated mice once with protein emulsified in TitermaxGold. The mice that were vaccinated with DNA and protein (group C) developed a significant splenic IgG+ B cell fraction (in addition to a large iIN IgG+ B cell fraction). If no protein is available to for boost immunizations, mice can be boosted with cells expressing the antigen or virus-like particles expressing the antigen.

In conclusion, DNA vaccination via DNA tattooing is an effective and robust vaccination strategy to induce an antigen specific humoral immune response. The mice that were vaccinated with only DNA (group A) developed a detectable IgG+ B cell fraction.

Example 6

Construction of Eukaryotic Vectors for the Efficient Production of Single VL Bispecific Human Monoclonal Antibodies One aspect of the present invention concerns the possibility of using sequence information from VH gene frequency analysis and/or HCDR3 heat maps to generate panels of antibodies in a desirable therapeutic format and screen those antibodies for binding and or functional activity. One such format is a bispecific IgG molecule. Conventional IgG molecules are comprised of two identical heavy- and two identical light chains. Heavy chains are polypeptides made up from separate domains: a VH region for antigen recognition, the CH1 domain, the hinge region, the CH2 domain and the CH3 domain. Pairing of the heavy chains to form a homodimer is the result of high affinity interactions between the CH3 domains, where after covalent coupling of the two heavy chains results from disulfide bridge formation between cysteines in the hinge region of the heavy chains.

The CH3 region has been used to introduce amino acid substitutions that inhibit the formation of homodimers (pairing of heavy chains with an identical CH3 region) while promoting heterodimerization (pairing of 2 different heavy chains with complementary, engineered CH3 regions). This has resulted in efficient heterodimer formation upon co-expression of CH3 engineered heavy chains (Gunasekaran et al., 2010; WO2006/106905; WO2009/089004).

In this example, we have constructed and tested expression vectors for the efficient production of human bispecific single VL antibodies. The overall strategy is that genetic constructs encoding 2 different antibodies are co-transfected into a single cell. By using complementary engineered CH3 regions for the 2 different heavy chains, formation of heterodimers (bispecific antibodies) is favored over the formation of homodimers (monospecific antibodies). Previously, it was shown that the combination of K409D:K392D in the CH3 domain of one heavy chain in combination with D399'K: E356'K in the CH3 domain of the second chain (thus, so-called complementary engineered CH3 regions) drives the heterodimerization of human heavy chain constant regions in an engineered bispecific molecule (Gunasekaran 2010). We used to the same amino acid pairs in the CH3 regions of constructs encoding single VL IgG antibodies to establish whether this would result in the efficient production of bispecific single VL human IgG monoclonal antibodies through heterodimerization.

The rearranged single IGVκ1-39 VL gene was cloned into a eukaryotic expression vector that contains the human gamma1 and kappa constant regions essentially as described (Throsby et al., 2008/de Kruif et al., 2009). Vector MV1201 contains DNA encoding a CH3 domain with the K409D: K392D amino acid substitutions in combination with a VH region encoding a human single VL monoclonal antibody specific for fibrinogen. Vector MV1200 contains DNA encoding a CH3 domain with the D399'K:E356'K amino acid substitutions in combination with a VH region encoding a human single VL monoclonal antibody specific for thyroblobulin (Gunasekaran et al., 2010/de Kruif et al., 2009).

Figure 8:
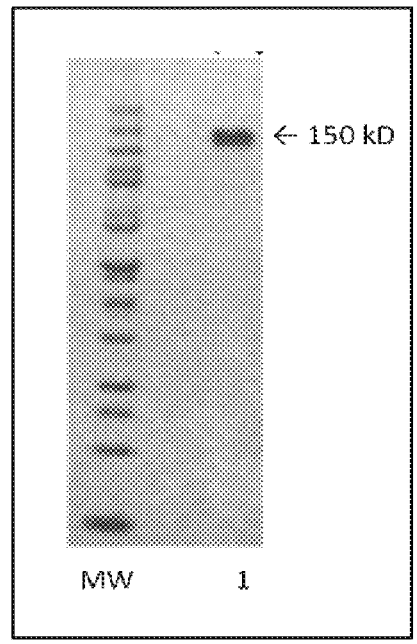
FIG. 8 shows a native SDS-PAGE analysis of a protein A purified single VL human bispecific antibody preparation. MW: molecular weight. Lane 1, anti-thyroglobulin×anti-fibrinogen bispecific.

MV1201 and MV 1200 were co-transfected into HEK293T cells and transiently expressed as described (de Kruif et al., 2009). After 13 days, supernatants were harvested and purified by protein A affinity chromatography using standard protocols. The protein A-purified IgG was analyzed by SDS-PAGE under reduced and non-reducing conditions; staining of proteins in the gel was carried out with colloidal blue. The results of this experiment are shown in FIG. 8 Under non-reducing SDS-PAGE, a single band with molecular weight of 150 kD was detected, showing that with these constructs hetero- and or homodimers were formed and no IgG half molecules consisting of a non-paired heavy/light chain combination.

Figure 9:
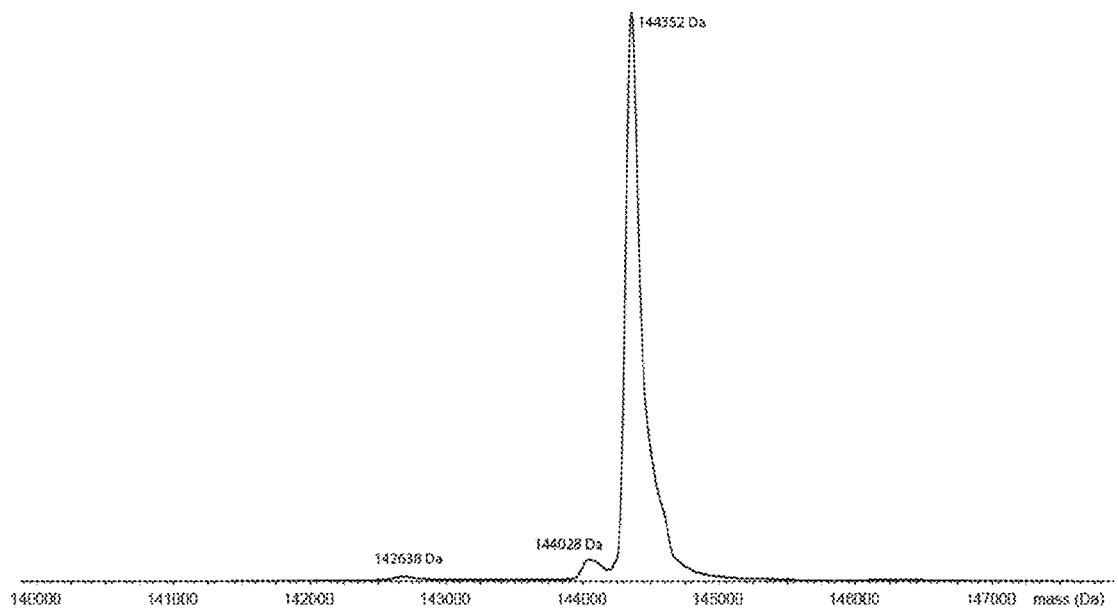
FIG. 9 depicts a native mass spectrometry analysis of a protein A purified single VL human bispecific antibody for fibrinogen and thyroglobulin produced by co-transfection of HEK293 cells. The main peak of 144352 Da is the heterodimeric bispecific IgG species (96% of total IgG); whereas the minor peaks of 144028 Da (3% of total IgG) and 142638 Da (1% of total IgG) are the homodimeric parental IgG species.

After protein A purification, mass spectrometry was used to identify the different IgG species produced by the transiently transfected cells. As shown in FIG. 9, the supernatant contained 96% heterodimeric IgG and 3% and 1% of each of the parental monoclonal antibodies. Thus, these protein A supernatants can be immediately used for screening of binding activity and/or functional assays of bispecific antibodies.

Example 7

Generation of Bispecific Antibodies Specific for ErbB1 and ErbB2 Tumor Antigens and Analysis of Tumor Cell Killing and Inhibition of Tumor Cell Proliferation Erbb1 and ErbB2 are growth factor receptors that play an important role in tumor development and progression. Combinations of monoclonal antibodies against ErbB1 and ErbB2 have shown synergistic effects in animal models of cancer (Larbouret et al., 2007) and therefore represent promising therapeutics for the treatment of cancer in humans. In this example, we demonstrate that, upon immunization, human monoclonal antibodies can be obtained from transgenic mice with a single human light chain through high throughput sequencing and creation of CDR3 heat maps and that combinations of ErbB1 and ErbB2 antibodies with additive and/or synergistic effect can be rapidly identified by in vitro screening.

Transgenic mice with a single human light chain are immunized with ErbB2 DNA and protein as described in example 5. Using the same protocols, another group of mice is immunized with ErbB1 DNA and proteins using the same procedures. For ErbB1 and ErbB2 immunized mice, spleens are isolated and the VH repertoire of IgG+ B cells is analyzed by high throughput sequencing as described in examples 1 and 2.

After construction of CDR3 heat maps, the top 100 VH sequence groups for each ErbB1 and ErbB2 immunized mice are selected for further analysis. For the collection of ErbB1 and ErbB2 VH sequences, VH sequences representative for each cluster, this is the VH gene that is present most frequently within a cluster, which may be a germline gene or a gene containing mutations, are cloned in an expression vector containing the single light chain and the CH3 mutation; ErbB1 VHs in MV1200 and ErbB2 VHs in MV1201. HEK293 cells are transiently transfected with all 2500 combinations (50 times 50) of cloned ErbB1 and ErbB2 VH sequence groups using the expression constructs that drive heterodimerization to form ErbB1×ErbB2 bispecific antibodies as described in example 6. After 13 days, culture supernatants are harvested and purified using protein A affinity chromatography. Purified IgG is used in functional assays of tumor cell killing and inhibition of tumor cell proliferation known in the art.

After identification of ErbB1×ErbB2 bispecific antibodies with potent anti-tumor activity, VH sequence collections present in the clusters that have an identical or similar CDR3 and that are used in the functional bispecific antibodies can be further deconvoluted using the same approach to find those VH members in the collection that give the most potent anti-tumor activity.

Example 8

Deep Sequencing and Diversity Analysis of HCDR3 from Samples Obtained from Splenic B Cells from Non-Immunized Versus Immunized Mice To demonstrate that the selective expansion of clones identified by unique HCDR3 sequences upon immunization can be analyzed by deep sequencing, splenic B cells from non-immunized and immunized mice were submitted to enrichment for B cells as described above. Nucleic acids were isolated and, where needed amplified as described above and cDNA was sent to Eurofins for high throughput sequencing.

Mice transgenic for huVκ1-39 and for a human heavy chain (HC) minilocus were immunized with protein only (fused to Fc) or by using alternating protein and cellular immunizations (with cells expressing the same antigen on their surface). cMet and EGFR were used as antigens in this example (two animals per group):

Group A: cMet-Fc in Titermax Gold adjuvant (TMG) on days 0, 14 and 28, and cMet-Fc in PBS on day 47.

Group B: cMet-Fc in TMG on days 0, 14 and 28, MKN45 cells in PBS on day 49, and cMet-Fc in PBS on day 64.

Group C: EGFR-Fc in TMG on days 0, 14 and 28, and EGFR-Fc in PBS on day 54.

Group D: EGFR-Fc in TMG on days 0, 14 and 28, A431 cells in PBS on day 49, and EGFR-Fc in PBS on day 64.

Doses used were 20 μg protein in 125 μl TMG, 20 μg protein in 200 μl PBS and 2×10E6 cells in 200 μl PBS. Non-immunized transgenic mice were around the same age as immunized mice at sacrifice (16 weeks, three mice in total).

Spleens were collected from all mice (for immunized mice three days after the last immunization) and processed as described in Example 2. To be able to sequence many different samples in a mixture at reduced cost, a material identification (MID) tag specific for each mouse was added at the 5' end of each primer used in PCR amplification of cDNA together with the SMART sequence (as detailed in Example 2). MID tag addition thus allowed pooling of material from several mice after PCR amplification and before 454-sequencing. Primers for amplification were thus adjusted to include MID tag complementary sequences (Table 3).

For non-immunized mice, spleen cell suspensions were enriched for B-cells using anti-CD 19 Microbeads (Miltenyi Biotec, cat. no. 130-052-201) and then sorted by flow cytometry to isolate mature, antigen-naive B cells expressing IgM or IgD. This was done by sorting for CD19-positive, B220-positive, huVκ1-39-positive and mouse light chain-negative B-cells and discriminating these in IgM-positive or IgD-positive cell fractions. In reverse primers used for cDNA synthesis, sequences were used that annealed to either IgM or IgD coding sequences. To be able to perform pooled sequencing for different samples, MID tags were used here to identify material from different samples (Table 14).

TABLE 13

Primers used for deep sequencing material from immunized mice (one MID tag per mouse).

| MID tag | Sequence* | SEQ ID NO: | Primer type | Primer name |
|---|---|---|---|---|
| MID-01 | ACGAGTGCGTAAGCAGTGGTATCAACGCAGAGT | 131 | Forward | SMART-MID1-fw |
| MID-01 | ACGAGTGCGTCAGGGGCCAGTGGATAGAC | 132 | Reverse | mIgG-CH1-MID1-rev |
| MID-02 | ACGCTCGACAAAGCAGTGGTATCAACGCAGAGT | 133 | Forward | SMART-MID2-fw |
| MID-02 | ACGCTCGACACAGGGGCCAGTGGATAGAC | 134 | Reverse | mIgG-CH1-MID2-rev |
| MID-03 | AGACGCACTCAAGCAGTGGTATCAACGCAGAGT | 135 | Forward | SMART-MID3-fw |
| MID-03 | AGACGCACTCCAGGGGCCAGTGGATAGAC | 136 | Reverse | mIgG-CH1-MID3-rev |
| MID-04 | AGCACTGTAGAAGCAGTGGTATCAACGCAGAGT | 137 | Forward | SMART-MID4-fw |
| MID-04 | AGCACTGTAGCAGGGGCCAGTGGATAGAC | 138 | Reverse | mIgG-CH1-MID4-rev |
| MID-05 | ATCAGACACGAAGCAGTGGTATCAACGCAGAGT | 139 | Forward | SMART-MID5-fw |
| MID-05 | ATCAGACACGCAGGGGCCAGTGGATAGAC | 140 | Reverse | mIgG-CH1-MID-rev |
| MID-06 | ATATCGCGAGAAGCAGTGGTATCAACGCAGAGT | 141 | Forward | SMART-MID6-fw |
| MID-06 | ATATCGCGAGCAGGGGCCAGTGGATAGAC | 142 | Reverse | mIgG-CH1-MID6-rev |
| MID-07 | CGTGTCTCTAAAGCAGTGGTATCAACGCAGAGT | 143 | Forward | SMART-MID7-fw |
| MID-07 | CGTGTCTCTACAGGGGCCAGTGGATAGAC | 144 | Reverse | mIgG-CH1-MID7-rev |
| MID-08 | CTCGCGTGTCAAGCAGTGGTATCAACGCAGAGT | 145 | Forward | SMART-MID7-fw |
| MID-08 | CTCGCGTGTCCAGGGGCCAGTGGATAGAC | 146 | Reverse | mIgG-CH1-MID8-rev |

*The MID tag sequence is underlined; the SMART sequence is in bold; the IgG constant HC sequence in regular type.

TABLE 14

Primers used for deep sequencing material from non-immunized mice (one MID tag per cell population per mouse).

| Cell fraction* | MID tag | Sequence** | SEQ ID NO: | Primer type | Primer name |
|---|---|---|---|---|---|
| IgM$^{HIGH}$ B cells mouse 1 | MID-04 | AGCACTGTAGAAGCAGTGGTATCAACGCAGAGT | 137 | Forward | SMART-MID4-fw |
| IgM$^{HIGH}$ B cells mouse 1 | MID-04 | AGCACTGTAGGGCCACCAGATTCTTATCAGAC | 147 | Reverse | mouse IgM-CH1-MID4-rev |
| IgD$^{HIGH}$ B cells mouse 1 | MID-05 | ATCAGACACGAAGCAGTGGTATCAACGCAGAGT | 139 | Forward | SMART-MID5-fw |
| IgD$^{HIGH}$ B cells mouse 1 | MID-05 | ATCAGACACGCAGTTCTGAGGCCAGCACAGTG | 148 | Reverse | mouse IgD-CH1-MID5-rev |
| IgM$^{HIGH}$ B cells mouse 2 | MID-10 | TCTCTATGCGAAGCAGTGGTATCAACGCAGAGT | 149 | Forward | SMART-MID10-fw |
| IgM$^{HIGH}$ B cells mouse 2 | MID-10 | TCTCTATGCGGGCCACCAGATTCTTATCAGAC | 150 | Reverse | mouse IgM-CH1-MID10-rev |
| IgD$^{HIGH}$ B cells mouse 2 | MID-11 | TGATACGTCTAAGCAGTGGTATCAACGCAGAGT | 151 | Forward | SMART-M D11-fw |
| IgD$^{HIGH}$ B cells mouse 2 | MID-11 | TGATACGTCTCAGTTCTGAGGCCAGCACAGTG | 152 | Reverse | mouse IgD-CH1-MID11-rev |
| IgM$^{HIGH}$ B cells mouse 3 | MID-16 | TCACGTACTAAAGCAGTGGTATCAACGCAGAGT | 153 | Forward | SMART-MID16-fw |
| IgM$^{HIGH}$ B cells mouse 3 | MID-16 | TCACGTACTAGGCCACCAGATTCTTATCAGAC | 154 | Reverse | mouse IgM-CH1-MID16-rev |
| IgD$^{HIGH}$ B cells mouse 3 | MID-17 | CGTCTAGTACAAGCAGTGGTATCAACGCAGAGT | 155 | Forward | SMART-MID17-fw |

TABLE 14-continued

Primers used for deep sequencing material from non-immunized mice
(one MID tag per cell population per mouse).

| Cell fraction* | MID tag | Sequence** | SEQ ID NO: | Primer type | Primer name |
|---|---|---|---|---|---|
| IgD<sup>HIGH</sup> B cells mouse 3 | MID-17 | <u>CGTCTAGTAC</u>CAGTTCTGAGGCCAGCACAGTG | 156 | Reverse | mouse gD-CH1-MID17-rev |

*B cells selected for expression of only huVK1-39 LC.
**The MID tag sequence is underlined; the SMART sequence is in bold; the IgD or IgM constant sequences in regular type.

For analysis of the sequencing results, custom designed algorithms were used for VH gene identification and alignment of HCDR3 regions. Briefly, raw sequence data were imported into a dedicated computer program, which translated all nucleotide sequences into six potential protein reading frames, each of which was then submitted to the following sequential filter criteria to find correct and complete human VH genes:

Sequences shorter than 75 amino acids were rejected as this was considered as the minimal length to positively identify VH genes.

Sequences without two canonical cysteines were rejected as these were used to identify VH genes and reading frames.

Frameworks 1 to 4 were searched for based on homology with VH genes in a database. If one or more of these frameworks were not found, the sequence was rejected.

CDR1, 2 and 3 were identified based on the identified framework regions. The sequence was rejected when a stop codon was present in one or more of the CDRs.

Sequences that passed these criteria were classified as annotated VH sequences. All selected VH sequences were then submitted to another algorithm to group them into clusters with a 100% identical HCDR3.

These data resulted in annotated VH genes and these VH genes were clustered based on HCDR3 sequence. To analyze the selective expansion of HCDR3 regions in VH genes in immunized versus non-immunized mice, the results were tabulated and expressed as the ratio of annotated VH regions over clusters with identical HCDR3 regions (Table 15). For ease of interpretation, results for separate B cell fractions from non-immunized mice were pooled so that the ratio could analyzed for total mature, antigen-naïve B cells.

reflected in VH/cluster ratios near 1.0. This implies that in these mice there was no trigger for selective expansion of B cells that would carry VHs with certain HCDR3 regions, as would be expected in the absence of an immunogenic stimulus. In contrast, in immunized mice the ratio of VH regions over clusters with identical HCDR3 is, although variable between individual mice, much higher and VH/cluster ratios range from 3.2 to 20.0. Thus, in immunized mice a large fraction of HCDR3 sequences is present in high frequency in the repertoire probably as a result of clonal expansion of antigen-reactive B cells due to immunization of the mice. This indicates that the high frequency VH regions are likely the clones that are specific for the antigen of interest and suggests that mining these VH genes and expressing them as Fab or IgG together with the common light chain will likely render antibodies with specificity for the antigen. Data that this is indeed the case are shown in Example 9. Functionality of these antigen-specific antibodies can subsequently be tested in functional assays.

Example 9

Deep Sequencing of VH Repertoires and HCDR3 Heat Map Generation from Immunized Mice Expressing a Common Light Chain As is clear from Example 8, a large fraction of HCDR3 sequences is present at a high frequency in the VH repertoire of immunized mice carrying a common light chain as opposed to non-immunized mice. In the present example, the repertoire of these most frequently used VH genes from immunized mice was mined to find antigen-specific heavy

TABLE 15

Deep sequencing data from immunized versus non-immunized mice.

| Immunization | Analyzed B cell population | Annotated VH regions | Clusters with identical HCDR3 | Ratio VH/clusters |
|---|---|---|---|---|
| None | Total mature B cells* | 39,626 | 30,716 | 1.3 |
| None | Total mature B cells* | 6,102 | 5,676 | 1.1 |
| None | Total mature B cells* | 9,128 | 8,437 | 1.1 |
| cMet protein | Total B cells | 34,327 | 2,757 | 12.5 |
| cMet protein | Total B cells | 90,049 | 4,511 | 20.0 |
| cMet protein & cells | Total B cells | 19,645 | 3,233 | 6.1 |
| cMet protein & cells | Total B cells | 75,838 | 4,557 | 16.6 |
| EGFR protein | IgG<sup>+</sup> B cells | 46,924 | 4518 | 10.4 |
| EGFR protein | IgG<sup>+</sup> B cells | 3,799 | 1201 | 3.2 |
| EGFR protein & cells | Total B cells | 60,979 | 3526 | 17.3 |
| EGFR protein & cells | Total B cells | 43,631 | 2452 | 17.8 |

*B cells expressing either IgM or IgD.

From table 15 it can readily be observed that the number of clusters with identical HCDR3 in non-immunized mice is in the order of the number of annotated VH genes, which is chain-derived binding domains which upon combination with the common light chain will render functional antibodies against the target of interest.

Material from mice carrying the huVκ1-39 transgene and a human HC minilocus upon immunization with cMet or EGFR (protein-Fc, or protein-Fc alternating with cells expressing the respective proteins at their surface; two mice per strategy so eight in total) was generated and processed as described in Example 8.

Deep sequencing and VH repertoire analysis including clustering based on HCDR3 identity revealed a total 287920 sequences which could be grouped into 813 unique clusters. All sequences in a cluster were derived from the same germline VH gene. Clusters that contained more than 50 VHs (with identical HCDR3 at the amino acid level but otherwise different VH regions) were collected into one database for repertoires from all eight mice. This was done since (limited) overlap of HCDR3 sequences was observed between the repertoires of the eight mice. VH sequences were then ranked on HCDR3 length and HCDR3 sequence identity. Next, HCDR3 sequences were further grouped based on the likelihood of a unique VDJ (i.e. if HCDR3 in different clusters contained <2 amino acids difference then they were considered part of the same cluster and were grouped together). This process was performed manually in an Excel worksheet but could be better performed on the basis of HCDR3 nucleotide sequence alignment. Tools to facilitate this are in development. This resulted in a total of 399 clusters with the same number of total sequences. The clusters were then aligned based on their size (i.e. total number of sequences in the cluster) and the top ~100 clusters for each target selected. This resulted in a total of 228 unique sequences: 134 from cMet-immunized mice and 94 from EGFR-immunized mice. Finally to select the nucleotide sequence to be recloned as an IgG from each cluster, the VH amino acid sequence alignment for each cluster was analyzed and the most frequent sequence in the cluster was chosen for recloning.

The corresponding nucleotide sequences were retrieved, modified to contain restriction sites for cloning into an expression vector and for removal of excessive restriction sites by silent mutation and then synthesized according to procedures known to the skilled person. Synthesized genes were cloned in bulk into a vector for expression in human IgG1 format including the huVκ1-39 common light chain. Of the rendered clones, 400 clones were picked by standard procedures and sequenced, and bulk cloning was repeated for missing or incorrect sequences until >90% of the 228-repertoire was retrieved. DNA was recovered and transiently transfected into an antibody production cell line. Methods used to modify sequences, synthesize DNA, clone, sequence and produce IgG by transfection are all known in the art.

IgG concentration of productions was determined using Octet technology (ForteB10) according to the manufacturer's instructions for basic quantitation with a protein A sensor chip with regeneration (ForteB10, cat. no. 18-0004/-5010/-5012/-5013). The 228 IgG were subsequently submitted to testing for antigen specific binding by ELISA at a concentration of 5 µg/ml. Of the tested sequences, 16 out of 110 (15%) were found to specifically bind to cMet and 6 out of 88 (7%) to EGFR. The other frequent clusters represent, for the large majority, antibodies that are directed to the Fc part of the antigen. It should be noted that the Fc-tail of the Fc-fusion proteins can be particularly immunogenic (Ling 1987, Immunology, vol 62, part 1, pp 1-6). Since these sequences were derived from material of mice immunized with Fc-fusion proteins in adjuvant, a large part of the humoral response will be directed to the Fc-tail (see Example 3 and 4). Binding to cells expressing the antigen on their surface was only done for IgG with binding domains derived from mice that were immunized with protein and cells, using cMet-expressing MKN45 cells or EGFR-expressing A431 cells. All IgG from cell-immunized mice that stained cMet or EGFR in ELISA also stained cells expressing the respective antigens (data not shown). It is expected that upon immunization with pure antigen such as via DNA tattoo, the percentage of antigen-specific clones will be further increased.

Figure 10:
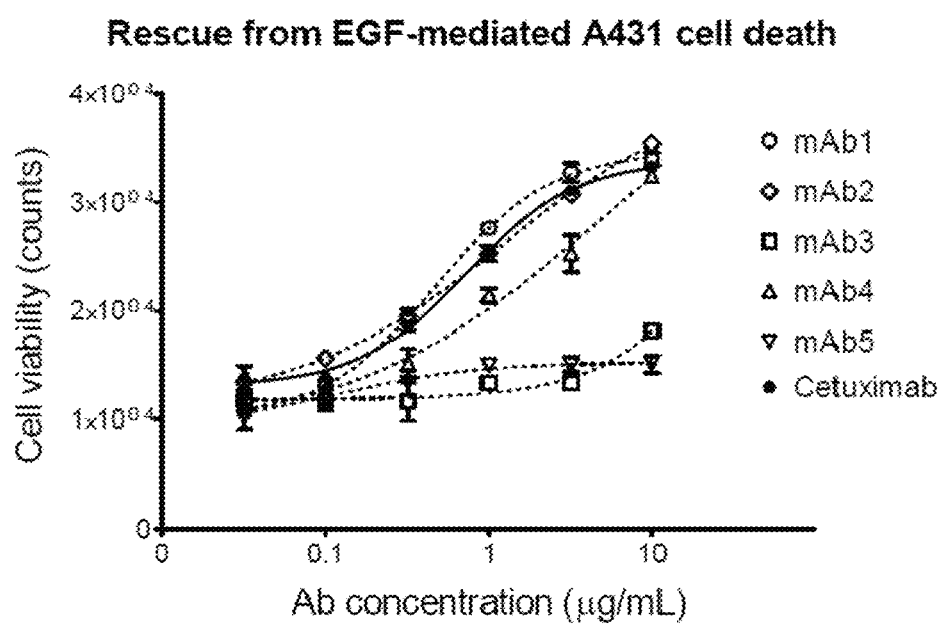
FIG. 10 is a graph showing the potency of EGFR-specific mAb to rescue A431 cells from EGF-induced cell death.

To functionally characterize the EGFR-specific IgG, these were tested for their potency to inhibit EGF-induced cell death of A431 cells (Gulli et al. 1996, Cell Growth Diff 7, p. 173-178). Of the 5 tested anti-EGFR mAbs, 3 were shown to inhibit EGF-induced A431 cell death (FIG. 10). The cMet-specific IgG were tested for functionality by determining their capacity to compete with several benchmark antibodies obtained from (patent) literature for binding to cMet in a binding competition ELISA. Briefly, 96-wells plates were coated with cMet-Fc and then incubated with an excess of one of several bench mark antibodies. Subsequently, tagged cMet-specific binders were added, followed by a peroxydase-labeled detection antibody that recognized bound cMet binders. The latter was detected using TMB as a substrate. Of the 10 tested cMet mAbs, 7 were demonstrated to compete for cMet binding with bench mark antibodies.

Thus, by using deep sequencing methods a broad panel of diverse antigen-specific VHs can be identified representing diverse VH usage, diverse HCDR3, and clonal maturation.

REFERENCES

Babcook J S, Leslie K B, Olsen O A, Salmon R A, Schrader J W. A novel strategy for generating monoclonal antibodies from single, isolated lymphocytes producing antibodies of defined specificities. Proc Natl Acad Sci USA. 93:7843-8 (1996).

Banchereau, J., de Paoli, P., Valle, A., Garcia, E. & Rousset, F. Long-term human B cell lines dependent on interleukin-4 and antibody to CD40. Science 251, 70-72 (1991).

Bins, A. D., et al., A rapid and patent DNA vaccination strategy defined by in vivo monitoring of antigen expression. Nat Med 11:899-904 (2005).

Boder, E. T. & Wittrup, K. D. Yeast surface display for screening combinatorial polypeptide libraries. Nat. Biotech. 15, 553-557 (1997).

Cobaugh, C. W., Almagro, J. C., Pogson, M., Iverson, B. & Georgiou, G. Synthetic antibody libraries focused towards peptide ligands. J. Mol. Biol. 378, 622-633 (2008).

Chao, G. et al. Isolating and engineering human antibodies using yeast surface display. Nat. Protoc. 1, 755-768 (2006).

Al-Lazikani, B., Lesk, A. M. & Chothia, C. Standard conformations for the canonical structures of immunoglobulins. J. Mol. Biol. 273, 927-948 (1997).

Clackson, T., Hoogenboom, H. R., Griffiths, A. D. & Winter, G. Making antibody fragments using phage display libraries. Nature 352, 624-628 (1991).

Clark. Antibody humanization: a case of the 'Emperor's new clothes'? Immunol Today, 21:397-402 (2000).

Crowe Jr. Recent advances in the study of human antibody responses to influenza virus using optimized human hybridoma approaches. Vaccine 27 (Suppl 6), G47 (2009)

Ettinger et al. IL-21 induces differentiation of human naive and memory B cells into antibody-secreting plasma cells. J. Immunol. 175, 7867-7879 (2005).

Feldhaus, M. J. et al, Flow-cytometric isolation of human antibodies from a nonimmune Saccharomyces cerevisiae surface display library. Nat. Biotechnol. 21:163-470 (2003).

Fuchs, P., Breitling, F., Dubel, S., Seehaus, T. 84 Little, M. Targeting recombinant antibodies to the surface of Escherichia-coli—fusion to a peptidoglycan associated lipoprotein. Biotechnology 9:1369-1372 (1991).

Ge X, Mazor Y, Hunicke-Smith S P, Ellington A D, Georgiou G: Rapid construction and characterization of synthetic antibody libraries without DNA amplification. Biotechnol Bioeng 106:347-357 (2010).

Good, K. L., Bryant, V. L. & Tangye, S. G. Kinetics of human B cell behavior and amplification of proliferative responses following stimulation with IL-21. J. Immunol. 177:5236-5247 (2006).

Green, L. L. et al. Antigen-specific human monoclonal antibodies from mice engineered with human Ig heavy and light chain YACs. Nat. Genet. 7:13-21 (1994).

Glanville J, Zhai W, Berka J, Telman D, Huerta G, Mehta G R, Ni I, Mei L, Sundar P D, Day G M R et al.: Precise determination of the diversity of a combinatorial antibody library gives insight into the human immunoglobulin repertoire. Proc Natl Acad Sci USA 106:20216-20221 (2009).

Gunasekaran et al. J. biol. Chem. 285: 19637-46. (2010)

Harding F A, Stickler M M, Razo J, DuBridge R B. The immunogenicity of humanized and fully human antibodies: residual immunogenicity resides in the CDR regions. MAbs. 2:256-65 (2010).

Harvey, B. R. et al. Anchored periplasmic expression, a versatile technology for the isolation of high-affinity antibodies from Escherichia coli-expressed libraries. Proc. Natl. Acad. Sci. USA 101:9193-9198 (2004).

Hoogenboom, H. R. Selecting and screening recombinant antibody libraries. Nat. Biotechnol. 23, 1105-1116 (2005).

Ishii, K. J., et al., TANK-binding kinase-I delineates innate and adaptive immune responses ta DNA vaccines. Nature, 451:725-9 (2008).

Jacob, J., et al., Activity of DNA vaccines encoding self or heterolagaus Her-2ineu in Her-2 or neu transgenic mice. Cell Immunol. 240:96-106 (2006).

Jacob, 1. B., et al., Combining human and rat sequences in her-2 DNA vaccines blunts immune talerance and drives antitumor immunity. Cancer Res 70:119-28 (2010).

Jechlinger, W., Optimization and delivery of plasmid DNA for vaccination. Expert Rev Vaccines 5: 803-25 (2006).

Jiang X, Suzuki H, Hanai Y, Wada F, Hitomi K, Yamane T, Nakano H. A novel strategy for generation of monoclonal antibodies from single B cells using rt-PCR technique and in vitro expression. Biotechnol Prog. 22:979-88 (2006).

Jin A, Ozawa T, Tajiri K, Obata T, Kondo S, Kinoshita K, Kadowaki S, Takahashi K, Sugiyama T, Kishi H et al.: A rapid and efficient single-cell manipulation method for screening antigen-specific antibody-secreting cells from human peripheral blood. Nat Med 15:1088-1092 (2009).

Kato M, Sasamori E, Chiba T, Hanyu Y. Cell activation by CpG ODN leads to improved electrofusion in hybridoma production. J Immunol Methods. 2011 Aug. 22. [Epub ahead of print]

Kim, C. H. et al. Subspecialization of CXCR5+ T cells: B helper activity is focused in a germinal center-localized subset of CXCR5+ T cells. J. Exp. Med. 193: 1373-1381 (2001).

Köhler, G. & Milstein, C. Continuous cultures of fused cells secreting antibody of predefined specificity. Nature 256: 495-497 (1975).

de Kruif J, Kramer A, Visser T, Clements C, Nijhuis R, Cox F, van der Zande V, Smit R, Pinto D, Throsby M, Logtenberg T. Human immunoglobulin repertoires against tetanus toxoid contain a large and diverse fraction of high-affinity promiscuous V(H) genes. J Mol Biol. 387:548-58 (2009).

Kwakkenbos, M. J. et al. Generation of stable monoclonal antibody-producing B cell receptor-positive human memory B cells by genetic programming. Nat. Med. 16: 123-428 (2010).

Larbouret C, Robert B, Navarro-Teulon I, Thezenas S, Ladjemi M, Morisseau S, et al. In vivo therapeutic synergism of anti-epidermal growth factor receptor and anti-HER2 monoclonal antibodies against pancreatic carcinomas. Clin Cancer Res. 13:3356-62 (2007).

Lee, C. M. Y., Iorno, N., Sierro, F. & Christ, D. Selection of human antibody fragments by phage display. Nat. Protoc. 2: 3001-3008 (2007).

Li, L. H., Hui, S. W. Characterization of PEG-mediated electrofusion of human erythrocytes. Biophys. J. 67: 2361 (1994).

Ling et al. Immunology 1987, vol 6 part 1, 1-6

Lonberg, N. et al. Antigen-specific human antibodies from mice comprising four distinct genetic modifications. Nature 368: 856-859 (1994).

Love, J. C., Ronan, J. L., Grotenbreg, G. M., van der Veen, A. G. & Ploegh, H. L. A microengraving method for rapid selection of single cells producing antigen-specific antibodies. Nat. Biotechnol. 24: 703-707 (2006).

Manz, R. A., Hauser, A. E., Hiepe, F. & Radbruch, A. Maintenance of serum antibody levels. Annu. Rev. Immunol. 23: 367-386 (2005).

Mao H, Graziano J J, Chase T M, Bentley C A, Bazirgan O A, Reddy N P, Song B D, Smider V V. Spatially addressed combinatorial protein libraries for recombinant antibody discovery and optimization. Nat Biotechnol. 28:1195-202 (2010).

Mazor, Y., Blarcom, T. V., Mabry, R., Iverson, B. L. & Georgiou, G. Isolation of engineered, full-length antibodies from libraries expressed in Escherichia coli. Nat. Biotechnol. 25: 563-565 (2007).

Meijer, P.-J. et al. Isolation of human antibody repertoires with preservation of the natural heavy and light chain pairing. J. Mol. Biol. 358: 764-772 (2006).

Middendorp, S., G. M. Dingjan, and R. W. Hendriks, Impaired precursor B cell differentiation in Bruton's tyrosine kinase-deficient mice. J Immunol 168: 2695-703 (2002).

Mohapatra, S. & San Juan, H. Designer monoclonal antibodies as drugs: the state of the art. Exp. Rev. Clin. Immunol. 4: 305-307 (2008).

Ogunniyi A O, Story C M, Papa E, Guillen E, Love J C: Screening individual hybridomas by micro-engraving to discover monoclonal antibodies. Nat Protoc 4:767-782 (2009).

Persson, H., Lantto, J. & Ohlin, M. A focused antibody library for improved hapten recognition. J. Mol. Biol. 357: 607-620 (2006).

Pokorna, D., I. Rubio, and M. Muller, DNA-vaccination via tattooing induces stronger humaral and cellular immune responses than intramuscular delivery supported by molecular adjuvants. Genet Vaccines Ther. 6: 4 (2008).

Ponsel D, Neugebauer J, Ladetzki-Baehs K, Tissot K. High affinity, developability and functional size: the holy grail of combinatorial antibody library generation. Molecules. 16:3675-700 (2011).

Quaak, 5. G., et al., GMP production of pDfRMA IT for vaccination against melanoma in a phase I clinical trial. Eur J Pharm Biopharm, 70:429-38 (2008).

Ravn U, Gueneau F, Baerlocher L, Osteras M, Desmurs M, Malinge P, Magistrelli G, Farinelli L, Kosco-Vilbois M H, Fischer N: By-passing in vitro screening—next generation sequencing technologies applied to antibody display and in silico candidate selection. Nucleic Acids Res 38:e193 (2010).

Reddy S T, Ge X, Miklos A E, Hughes R A, Kang S H, Hoi K H, Chrysostomou C, Hunicke-Smith S P, Iverson B L, Tucker P W, Ellington A D, Georgiou G. Monoclonal antibodies isolated without screening by analyzing the variable-gene repertoire of plasma cells. Nat Biotechnol. 28:965-9 (2010).

Reddy S T, Georgiou G. Systems analysis of adaptive immunity by utilization of high-throughput technologies. Curr Opin Biotechnol. 4:584-9 (2011).

Ruuls S R, Lammerts van Bueren J J, van de Winkel J G, Parren P W. Novel human antibody therapeutics: the age of the Umabs. Biotechnol J. 3:1157-71 (2008).

Schaffitzel, C., Hanes, J., Jermutus, L. & Plückthun, A. Ribosome display: an in vitro method for selection and evolution of antibodies from libraries. J. Immunol. Methods 231: 119-135 (1999).

Schmidlin H, Diehl S A, Blom B. New insights into the regulation of human B-cell differentiation. Trends Immunol. 30:277-85 (2009).

Shapiro-Shelef, M. & Calame, K. Regulation of plasma-cell development. Nat. Rev. Immunol. 5: 230-242 (2005).

Smith K, Garman L, Wrammert J, Zheng N-Y, Capra J D, Ahmed R, Wilson P C: Rapid generation of fully human monoclonal antibodies specific to a vaccinating antigen. Nat Protoc. 4:372-384 (2009.)

Stevenson, F. K., et al., DNA vaccines to attack cancer. Proc Natl Acad Sci. 101 Suppl 2: p. 14646-52 (2004).

Story C M, Papa E, Hu C-C A, Ronan J L, Herlihy K, Ploegh H L, Love J C: Profiling antibody responses by multiparametric analysis of primary B cells. Proc Natl Acad Sci USA 105:17902-17907 (2008).

Tajiri K, Kishi H, Tokimitsu Y, Kondo S, Ozawa T, Kinoshita K, Jin A, Kadowaki S, Sugiyama T, Muraguchi A: Cell-microarray analysis of antigen-specific B-cells: single cell analysis of antigen receptor expression and specificity. Cytometry 71:961-967 (2007).

Tiller T, Meffre E, Yurasov S, Tsuiji M, Nussenzweig M C, Wardemann H: Efficient generation of monoclonal antibodies from single human B cells by single cell RT-PCR and expression vector cloning. J Immunol Methods 329: 112-124 (2008).

Tokimitsu Y, Kishi H, Kondo S, Honda R, Tajiri K, Motoki K, Ozawa T, Kadowaki S, Obata T, Fujiki S et al.: Single lymphocyte analysis with a microwell array chip. Cytometry 71:1003-1010 (2007).

Throsby, M., Geuijen, C., Goudsmit, J., Bakker, A. Q., Korimbocus, J., Kramer, R. A, et al. Isolation and characterization of human monoclonal antibodies from individuals infected with West Nile virus. J. Virol. 80, 6982-6992 (2006).

Traggiai, E., Becker, S., Subbarao, K., Kolesnikova, L., Uematsu, Y., Gismondo, M. R., Murphy, B. R., Rappuoli, R., Lanzavecchia, A. An efficient method to make human monoclonal antibodies from memory B cells: potent neutralization of SARS coronavirus. Nat. Med. 10, 871 (2004).

Weeratna, R., Comanita, L., Davis, H. L. CPG ODN allows lower dose of antigen against hepatitis B surface antigen in BALB/c mice. Immunol. Cell Biol. 81: 59 (2003).

Whittington, P. J., et al., DNA vaccination controls Her-2+ tumors that are refractory to targeted therapies. Cancer Res, 68:7502-11 (2008).

Wrammert, J. et al. Rapid cloning of high-affinity human monoclonal antibodies against influenza virus. Nature 453: 667-671 (2008).

Wu, C., Hua Ying, Grinnell, C., Bryant, S., Miller, R., et. al., Simultaneous targeting of multiple disease mediators by a dual-variable-domain immunoglobulin Nature Biotechnology 25, 1290-1297 (2007).

Yu, X., McGraw, P. A., House, F. S., Crowe Jr., J. E. An optimized electrofusion-based protocol for generating virus-specific human monoclonal antibodies. J. Immunol. Methods 336, 142 (2008).

Zubler R H, Werner-Favre C, Wen L, Sekita K, Straub C. Theoretical and practical aspects of B-cell activation: murine and human systems. Immunol Rev. 99:281-99 (1987).

The invention claimed is:

1. A method for producing a population of antibodies which bind to an antigen, said method comprising:
   a) providing a population of B cells from one transgenic mouse immunized with said antigen,
      wherein said antigen is essentially pure,
      wherein said population of B cells comprises essentially all B cells obtained from one or more lymphoid organs of said immunized mouse,
      wherein said transgenic mouse expresses a single rearranged human antibody light chain variable region (VL) from a VL nucleic acid,
      wherein the single rearranged human VL nucleic acid is a rearranged IgVκ/IGJκ nucleic acid,
      wherein the IgVκ nucleic acid is a germline IgVκ gene and the IGJκ nucleic acid is a germline IGJκ gene,
      wherein the IgVκ/IGJκ nucleic acid is resistant to DNA rearrangements and somatic hypermutations,
      wherein said transgenic mouse expresses a human antibody heavy chain variable region (VH) repertoire from a repertoire of VH nucleic acids,
      said B cell population expressing a repertoire of VHs and a single rearranged human VL,
      said B cell population expressing a limited immunoglobulin light chain variable (VL) region repertoire,
   b) obtaining essentially all of the nucleic acids encoding antibody heavy chain variable (VH) regions from essentially all of said B cells, c) obtaining nucleotide sequences of essentially all obtained nucleic acids of step b),
d) determining the frequency of nucleotide sequences from step c) which encode VH regions with unique HCDR3 amino acid sequences,
e) selecting nucleic acids encoding VH regions comprising frequently occurring HCDR3 amino acid sequences identified in step d),
f) providing host cells, wherein each host cell comprises at least one vector comprising a nucleotide sequence encoding at least one VH region selected in step e) wherein each said host cell expresses the single rearranged human VL nucleic acid of step a) and at least one VH region selected in step e),
g) culturing said host cells from step f) and allowing for expression of said VL and VH regions, and
h) obtaining said population of antibodies from the cultured host cells of step g) which bind said antigen.

2. A method according to claim 1, further comprising amplification of nucleic acids encoding antibody heavy chain variable regions from the nucleic acids of step b).

3. A method according to claim 1, further comprising subjecting a sample of said cultured host cells expressing said VL and VH regions of step g) to at least one functional assay, and selecting at least one cell that expresses an antibody which binds said antigen.

4. A method according to claim 1, wherein said population of antibodies is of bispecific antibodies.

5. A method according to claim 1, wherein the germline IgVκ gene is IGκV1*39.

6. A method according to claim 1, wherein VH regions comprising at least the 20 most abundant HCDR3s are selected.

7. A method according to claim 6, wherein VH regions comprising the 200 most abundant HCDR3s are selected.

8. A method according to claim 1, further comprising preparing a mixture of antibodies using the antibodies obtained in step h).

9. A method according to claim 8, wherein the mixture of antibodies is of bispecific antibodies.

10. A method according to claim 1, wherein the transgenic mouse has been immunized with a nucleic acid encoding said antigen.

* * * * *